(12) United States Patent
Staunton et al.

(10) Patent No.: US 9,463,312 B2
(45) Date of Patent: Oct. 11, 2016

(54) DELIVERY ASSEMBLY FOR PERCUTANEOUSLY DELIVERING AND DEPLOYING AN ELECTRODE ARRAY AT A TARGET LOCATION, THE ASSEMBLY CAPABLE OF STEERING THE ELECTRODE ARRAY TO THE TARGET LOCATION

(75) Inventors: Douglas Staunton, Texas Township, MI (US); Timothy J. Bozung, Scotts, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 426 days.

(21) Appl. No.: 13/250,164

(22) Filed: Sep. 30, 2011

(65) Prior Publication Data

US 2012/0022551 A1    Jan. 26, 2012

Related U.S. Application Data

(63) Continuation of application No. PCT/US2010/029628, filed on Apr. 1, 2010.

(60) Provisional application No. 61/166,366, filed on Apr. 3, 2009.

(51) Int. Cl.
*A61B 19/00* (2006.01)
*A61N 1/05* (2006.01)
*A61B 17/34* (2006.01)

(52) U.S. Cl.
CPC ......... *A61N 1/0553* (2013.01); *A61B 17/3468* (2013.01); *A61B 2562/125* (2013.01)

(58) Field of Classification Search
CPC .............. A61B 2562/12; A61B 2562/0209; A61B 2562/04; A61B 2562/043; A61B 2562/046; A61B 2562/06; A61B 2562/063; A61B 2562/066; A61B 2562/16; A61B 2562/164; A61B 18/14; A61B 18/16; A61B 2018/1405; A61B 2018/142; A61B 2018/1432; A61B 2018/1465; A61B 2018/1467; A61B 2018/147; A61B 2018/1475; A61B 2018/1497; A61B 2018/162; A61B 2018/165; A61B 2018/167; A61N 1/042; A61N 1/0424; A61N 1/0452; A61N 1/0456; A61N 1/046; A61N 1/0464; A61N 1/0468; A61N 1/0476; A61N 1/0504; A61N 1/0551; A61N 1/0553; A61N 1/04; A61N 1/0472; A61N 1/05; A61N 1/054; A61N 1/0556; A61N 1/056; A61N 1/0563; A61N 1/06; A61N 1/0534; A61N 1/0536; A61N 1/0539; A61N 1/0546; A61N 1/0548; A61N 1/0587; A61N 1/0404; A61N 1/0444; A61N 1/0408; A61N 1/0502; A61N 1/0507; A61N 1/0512; A61N 1/0514; A61N 1/0517; A61N 1/0519; A61N 1/0521; A61N 1/0524; A61N 1/0543
USPC .................................. 606/129; 607/115–119
See application file for complete search history.

(56) References Cited

U.S. PATENT DOCUMENTS 5,397,342 A * 3/1995 Heil et al. .................... 607/129
5,441,483 A   8/1995 Avitall
(Continued)

FOREIGN PATENT DOCUMENTS

WO   2009111142 A2   9/2009

OTHER PUBLICATIONS

International Search Report and Written Opinion for PCT App No. PCT/US2010/029628, Jun. 2010.

*Primary Examiner* — Jonathan Miles
*Assistant Examiner* — Kendra Obu

(57) ABSTRACT

An electrode array and a delivery assembly. The array is wrapped around a flexible core part of the delivery assembly. A sheath, also part of the delivery assembly, is disposed over the array and core. Steering cables extend through the core or sheath. Once the delivery assembly-encased array is inserted in the body, the combination is advanced to the tissue over which the array is to be deployed. By pulling on the steering cables the array and assembly are steered into position. Once the array is in position, the sheath is retracted, the array deploys over the target tissue.

29 Claims, 35 Drawing Sheets

(56) References Cited

U.S. PATENT DOCUMENTS

| | | |
|---|---|---|
| 5,730,127 A | 3/1998 | Avitall et al. |
| 5,846,196 A * | 12/1998 | Siekmeyer et al. .......... 600/374 |
| 5,881,727 A | 3/1999 | Edwards et al. |
| 6,415,187 B1 | 7/2002 | Kuzma et al. |
| 7,177,702 B2 * | 2/2007 | Wallace et al. ............... 607/117 |
| 2002/0022873 A1 | 2/2002 | Erickson et al. |
| 2003/0069577 A1 | 4/2003 | Vaska et al. |
| 2004/0186543 A1 * | 9/2004 | King et al. ..................... 607/116 |
| 2004/0236395 A1 * | 11/2004 | Iaizzo et al. ................... 607/116 |
| 2006/0241717 A1 * | 10/2006 | Whitehurst et al. ............ 607/45 |
| 2008/0065182 A1 * | 3/2008 | Strother et al. ................ 607/115 |
| 2009/0293270 A1 | 12/2009 | Brindley et al. |
| 2010/0082041 A1 * | 4/2010 | Prisco ............................ 606/130 |

* cited by examiner

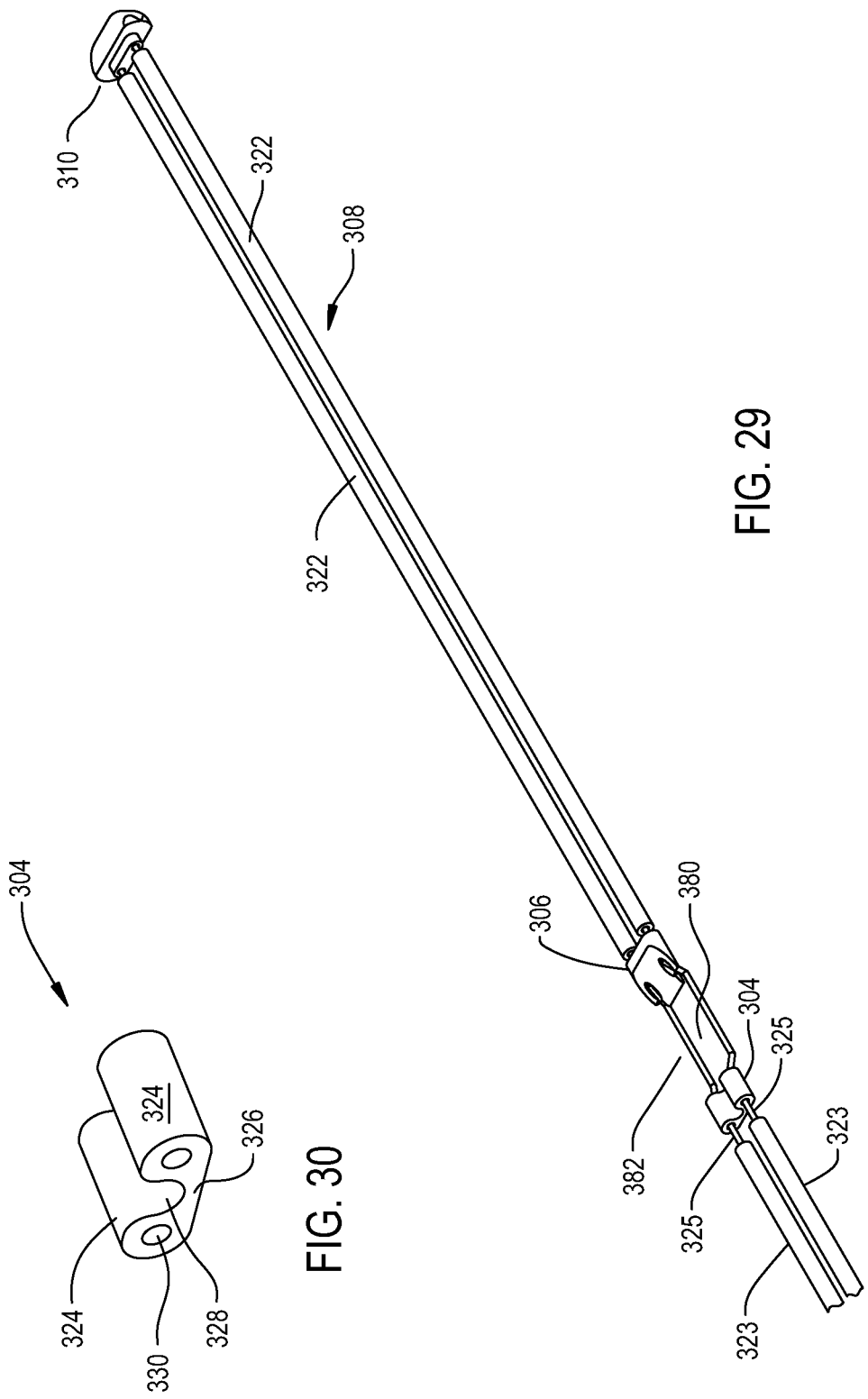

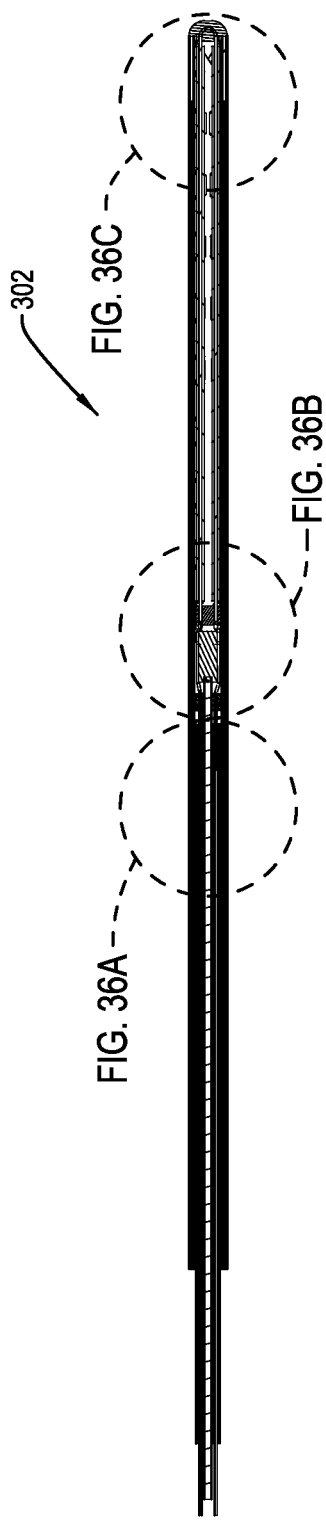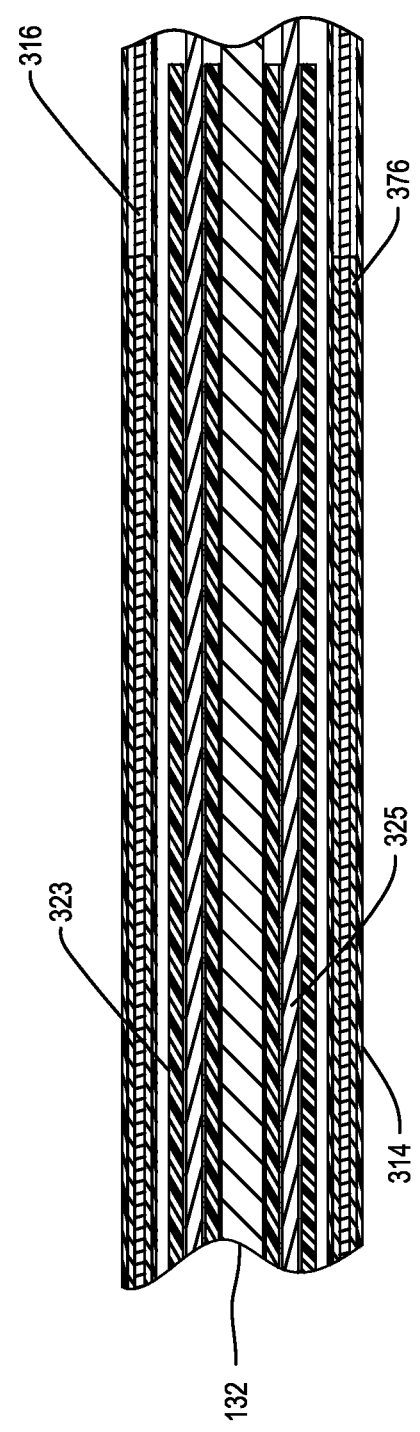
FIG. 36A
FIG. 36

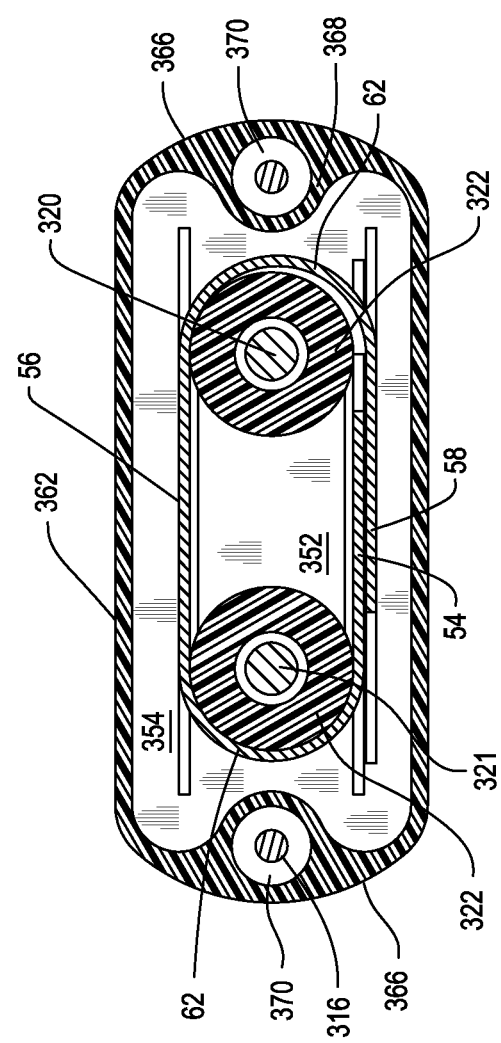

DELIVERY ASSEMBLY FOR PERCUTANEOUSLY DELIVERING AND DEPLOYING AN ELECTRODE ARRAY AT A TARGET LOCATION, THE ASSEMBLY CAPABLE OF STEERING THE ELECTRODE ARRAY TO THE TARGET LOCATION

FIELD OF THE INVENTION

This application is a continuation of US Pat. App. No. PCT/US2010/029628 filed 1 Apr. 2010. The '628 PCT Application claims priority from U.S. Provisional Pat. App. No. 61/166,366 filed 3 Apr. 2009.

FIELD OF THE INVENTION

This invention is generally related to an assembly and method for percutaneously or otherwise minimally invasively delivering an electrode array to a target location. The assembly and method of this invention are further capable of steering the electrode array to the target location and, once, at the location, deploying the electrode array so the array can be activated.

BACKGROUND OF THE INVENTION

There are a number of medical conditions for which it has been found that an effective therapy involves driving current through a section of the tissue of a patient. Often, the current is driven between the electrodes of an electrode array implanted in the patient. Generally, the electrode array includes a non-conductive carrier on which typically two or more electrodes are disposed. Once the electrode array is implanted, current is driven from at least one of the electrodes, through the adjacent tissue, to at least one of the other electrodes. The current flow through the tissue influences the tissue to accomplish a desired therapeutic result. For example, an electrode array positioned adjacent the heart may flow currents to stimulate the appropriate contraction and expansion of the heart muscles. There is an increasing interest in implanting electrode arrays adjacent neural tissue so that the resultant current flow induces a desired neurological or physical effect. In one known application, the current driven between the electrodes of an array placed on top of the dura in the vertebral column reduces the extent to which chronic pain signals are perceived by the brain. Alternatively, the array may be placed in a location where the current flow stimulates a feeling of stomach fullness as part of an appetite suppression/weight management therapy. In another application, the current is flowed to tissue or nerves associated with the bladder or the anal sphincter to assist in control of incontinence. Electrodes may be implanted in a paralysis victim to provide muscle control and/or a sense of feeling.

The Applicants' Patent Application No. PCT/US2009/33769, FOLDABLE, IMPLANTABLE ELECTRODE ARRAY ASSEMBLY AND TOOL FOR IMPLANTING SAME, filed 11 Feb. 2009, published as WO 2009/111142 and as U.S. Pat. No. 8,560,083, the contents of which are explicitly incorporated herein by reference, describes an electrode array that includes a frame on which plural electrodes are arranged in a row by column matrix. An advantage of this electrode array is that it allows current to be flowed between numerous different combinations of electrodes. Depending on which electrodes are operated to function as current sources and sinks, this array can be operated so that there are two or more current flows occurring simultaneously between different sets of electrodes. Once this array is deployed, the practitioner drives current between different combinations of electrodes. Current therefore flows through different sections of tissue. This allows the practitioner to determine between which electrodes, through which tissue, the current flow offers the greatest benefit and/or tolerable side effects. Once the optimal current flow path between the electrodes is determined, the array and its associated power supply are set to operate in this state. Should the electrodes shift or the clinical needs change, the array can be reset to accommodate these changes.

In comparison to other electrode arrays with lesser numbers of electrodes, the above-described array makes it possible to flow current through more sections of tissue and to selectively focus/diffuse the current flow. In contrast to an electrode array with a smaller number of electrodes, use of the above-described array increases the likelihood that the current flow can be set to provide desired therapeutic effects, with tolerable side effects.

Previously, there was a disadvantage of providing an electrode array with numerous individual electrodes that collectively occupy a large surface area. Specifically, owing to the size of these arrays, it was believed that the only way to position them against the tissue through which current is to be driven was to cut a relatively large incision in the patient to provide access to the target tissue. Typically, this incision is more than 3 cm in length and, often at least 5 cm in length. Once the incision is made, it is then usually necessary to retract at least a portion of the tissue overlying the target tissue. In some insertion procedures, removal of some of the overlying tissue is required. The electrode array was passed through the incision and placed against the target tissue. Once the electrode array was positioned, the incision was closed.

The electrode array of the incorporated by reference WO 2009/111142, is designed in part to be implanted in a patient without requiring such a large sized incision, tissue removal and the attendant trauma that results from these procedures. The Applicants' array of this incorporated-by-reference document is designed so that the electrodes are disposed on a frame formed from a superelastic material. A superelastic material is one that, after being subjected to appreciable bending or folding, returns to its initial state. Once this electrode array is formed, the assembly is then folded or rolled into a form that has a side-to-side width appreciably less than its width in the unfolded/unrolled state.

It has been proposed that this folded/rolled array then be placed in a deployment cannula. This electrode array-deployment cannula assembly is then fitted into a slightly wider insertion cannula. Once a portal, a puncture opening, is formed in the patient, the cannulae and electrode array are directed toward the surface of the tissue in the body against which the electrode array is to be deployed. The deployment cannula, with folded/rolled electrode array contained therein, is positioned over the target tissue. The deployment cannula is then retracted back into the insertion cannula while the electrode array is blocked from such movement. The retraction of the deployment cannula uncovers the folded/rolled electrode array. As a consequence of the electrode array being formed on the frame of superelastic material, the array, upon being uncovered, unfolds/unrolls back to its initial shape. The unfolded/unrolled array extends over the target tissue, the tissue through which it is believed current flow will provide the desired therapeutic effect.

A benefit of the above assembly is that only a relatively small portal is formed in the patient in order to position the cannulae-containing assembly in the vicinity of the target tissue. The need to form a large incision and possibly remove tissue in order to position the assembly, and the attendant trauma associated with such an incision is eliminated. It should similarly be appreciated that another advantage of avoiding having to make such a large incision in the patient is that it lessens the degree to which the internal tissue of the patient is exposed to the ambient environment and infection-causing agents in the environment. Thus, it should be appreciated that not having to make a large incision in a patient can reduce the patient's recovery time and risk of complications.

Likewise, the above procedure can typically be performed in less time than it takes to implant the electrode array through an open incision. This is consistent with one of the goals of modern surgical practice; minimizing the time the patient is held under anesthesia.

The above-described assembly and method for percutaneously deploying an electrode array eliminates having to form a large incision into the patient and the disadvantages associated with having to make such an incision. However, one limitation associated with this assembly and method is that it works best if the insertion cannula is positioned a relatively short distance from the target location over which the electrode array is to be deployed. Sometimes anatomic features or safety concerns makes it difficult, if not impossible, to place the cannulae at a location so that, upon deployment, the array seats over the target tissue. In these situations, ideally, it should be possible to advance the deployment cannula relative to the insertion cannula so the array is positioned over the target tissue. However, intervening tissue may block the advancement of the deployment cannula and array to the target tissue. This can make it difficult, if not impossible, to use the delivery assembly to deploy the electrode array.

SUMMARY OF THE INVENTION

This invention is directed to a new and useful assembly and method for percutaneously delivering and deploying an electrode array against target tissue through which the current sourced and/or sunk by the electrodes integral with the array is to be flowed. The assembly of this invention includes a flexible core around which an electrode array is folded or rolled. A sheath surrounds the core and electrode array to hold the electrode array in the folded over state. A steering assembly moves the core and array from side to side.

In some versions of the invention, the steering assembly is routed through the core to laterally displace the core. The displacement of the core results in a like displacement of the electrode array and the surrounding sheath. In some versions of the invention, the steering assembly is routed through the sheath to displace the distal head end of the sheath. Such movement results in a like displacement of the core and folded electrode array disposed within the sheath.

In some versions of the invention, the sheath is a sheet of material that is wrapped around the core and electrode array. In these versions of the invention, a retention assembly releasably holds the sheath in the wrapped state. Alternatively, the sheath may be a tube. This tube may be open ended or have a closed distal end that can be opened.

To deliver and deploy a cannula using the delivery assembly of this invention, often a portal is initially created in the patient. An access cannula is fitted in the patient. The sheath-encased electrode array and core are fitted into an access cannula and directed towards the distal end opening of the access cannula. Once the sheath-encased assembly exits the access cannula, the steering assembly is used to advance the assembly around obstructions. The assembly is positioned over the target tissue.

Once the sheath-encased assembly is positioned over the target tissue, the sheath is moved away from the folded-over electrode array. In versions of the invention in which a retention assembly holds the sheath in a closed, folded, state, this retention assembly is released. As a consequence of the electrode array releasing potential energy in the unfolding process, the wrapped sheath is forced open. The open sheath and core are then retracted. Alternatively, a tube-type sheath is simply retracted proximally away from the folded over electrode array. In these versions of the invention, as a consequence of the removal of the constraining sheath from over the folded over electrode array, the array unfolds. Once the electrode array unfolds, the core is removed.

This invention provides a means to insert an electrode array into a patient through an access cannula that is narrower in diameter than the width of the unfolded array and allows the array to be steered to the target tissue. Thus, this invention makes it possible to deploy a large width electrode array over target tissue using a percutaneous or otherwise minimally invasive procedure, where it might not otherwise be possible to position an array using this type of process.

BRIEF DESCRIPTION OF THE DRAWINGS

The invention is pointed out with particularity in the claims. The above and further features and advantages of this invention are better understood by reference to the following Detailed Description taken in conjunction with the accompanying drawings in which:

FIG. 29 is a perspective view of the assembled together spacers, core and tip of the delivery assembly of FIG. 27;

FIG. 30 is a perspective view of the proximal spacer of FIG. 29;

FIG. 36 is cross section of the array encased in the sleeve of the delivery assembly along the longitudinal axis of the assembly when viewed in a horizontal plane;

FIGS. 36A, 36B and 36C are enlarged views of sections of cross sectional view of FIG. 36;

FIG. 40 is a cross sectional view of the encased array when viewed along line 40-40 of FIG. 27.

DETAILED DESCRIPTION

I. Electrode Array

Figure 1:
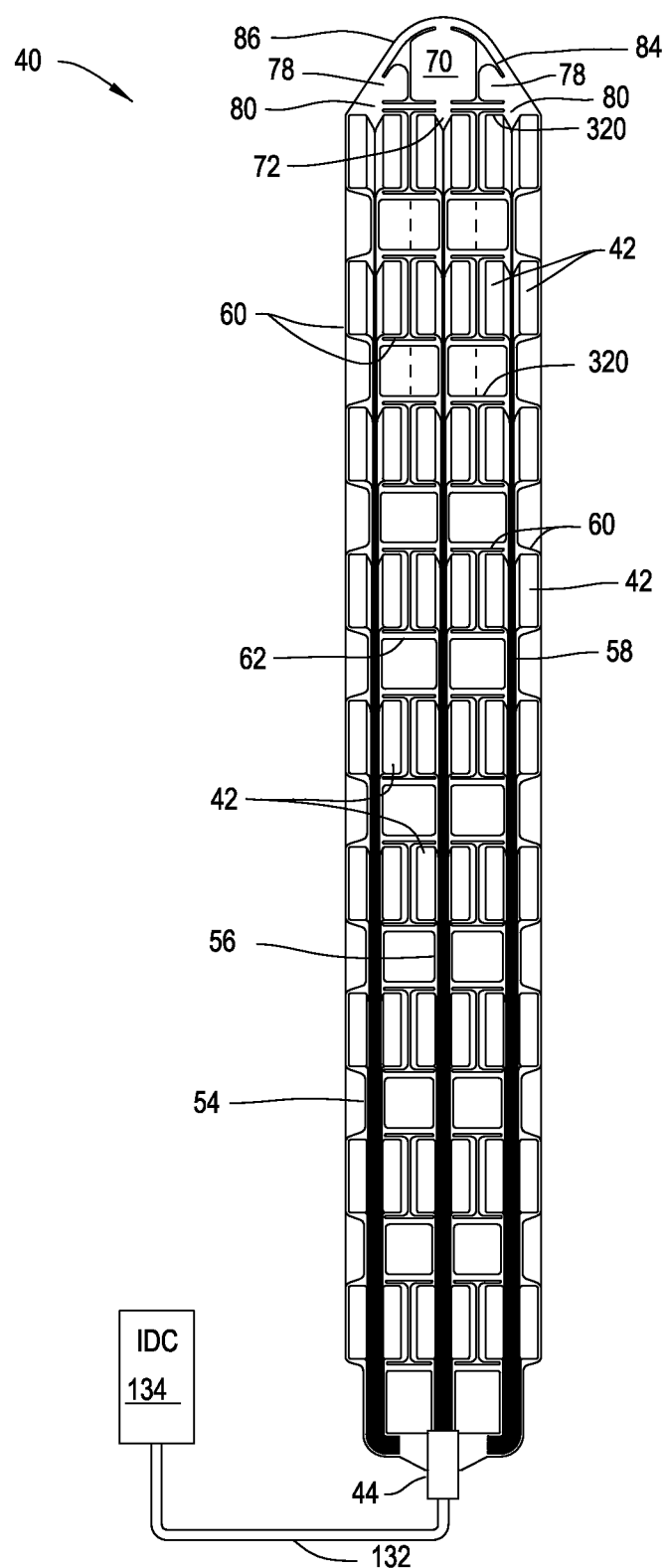
FIG. 1 is a plan view of an unfolded electrode array configured to be percutaneously delivered for deployment against target tissue.
Figure 2:
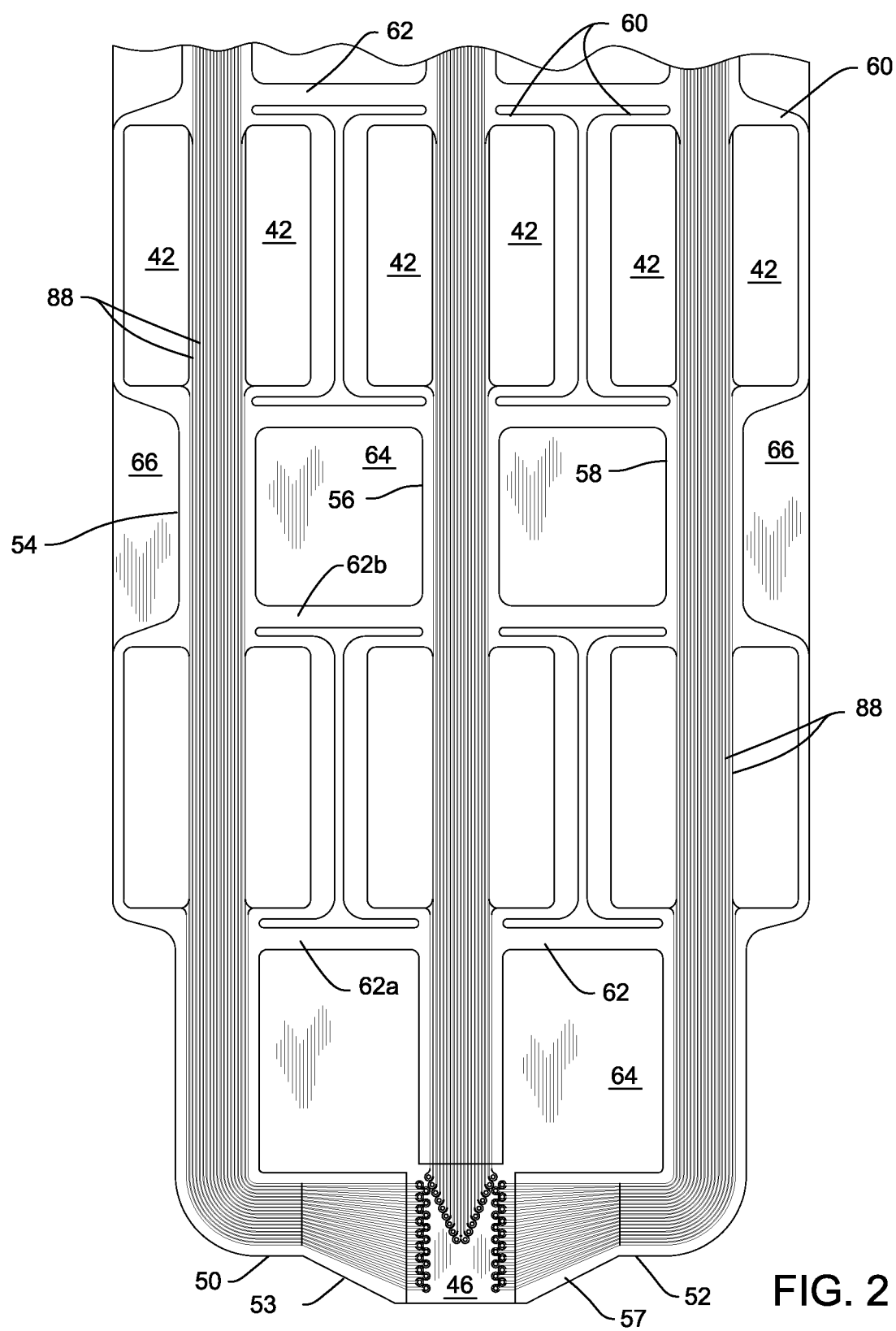
FIG. 2 is an enlarged plan view of the proximal end of the assembly of FIG. 1 wherein the drive module is absent from the terminal pad.

FIGS. 1 and 2 illustrate an electrode array 40 that can be percutaneously deployed over a section of tissue using the apparatus and method of this invention. Electrode array 40 includes a number of individual electrodes 42. The electrodes 42 are selectively tied to current sources and current sinks (not illustrated and not part of this invention). When the current sources and sinks are actuated, current flows from one or more electrodes 42 tied to the current source or sources, through regions of the tissue that underly the assembly 40. The current is driven through the tissue to the one or more electrodes 42 tied to the current sink or sinks. A drive module 44 selectively ties the electrodes 42 to the current sources and current sinks. Drive module 44 is located at the proximal end of the assembly 40. (Here, "proximal" means towards the end of the assembly at the bottom of FIG. 1; "distal" means towards the end of the assembly at the top of FIG. 1).

In FIG. 1, assembly 40 is shown active side up so electrodes 42 and drive module 44 can be seen. The "active" side of the assembly 40 is the side of the assembly on which the electrodes 44 are located. Opposite the active side, assembly 40 has a "passive" side.

In FIG. 2, drive module 44 is removed from the assembly 40 so the terminal pad 46 at the proximal end of the assembly can be seen. Terminal pad 46 is the substrate of the assembly 40 to which drive module 44 is attached. In many versions of the invention, the components forming assembly 40 are dimensioned so that drive module 42 extends rearwardly beyond the proximal end of terminal pad 46.

Three parallel bridges 54, 56 and 58 that are spaced apart side-by-side extend distally forward from terminal pad 46. The outer two bridges, bridges 54 and 58, are each formed with a leg, legs 50 and 52, respectively. Legs 50 and 52, which are coaxial and that extend outwardly from opposed sides of terminal pad 46. Bridges 54 and 58 extend perpendicularly forward, distally forward, from legs 50 and 52, respectively. Feet 53 and 57, respectively, connect legs 50 and 52 to terminal pad 46. Each foot 53 and 57 has a proximal end edge that tapers distally forward as the foot extends away from the adjacent side edge of terminal pad 46. Bridge 56, the center located bridge, extends forward from the distal end of terminal pad 46.

Plural tabs 60 extend outwardly from each bridge 54, 56 and 58. More particularly, at a number of spaced apart locations along the length of each bridge 54, 56 and 58, two tabs 60 extend outwardly from the opposed sides of the bridge. At least in the version of the invention depicted in FIG. 1, the tabs 60 are arranged in diametrically opposed pairs relative to the bridge 54, 56 or 58, from which the individual tabs extend. Electrode array 40 is further constructed so that at each longitudinal section on bridge 54 from which tabs 60 extend, tabs 60 also extend from the laterally adjacent longitudinal sections of bridges 56 and 58. Thus, in the illustrated version of the invention, tabs 60 are arranged in rows. In each row of tabs 60, two tabs extend outwardly from each bridge 54, 56 and 58. The rows of tabs 60 are longitudinally spaced apart from each other. In some versions of the invention, the separation between the distal end of one row of tabs and the proximal end of the distally adjacent row of tabs is between 1 to 10 mm. In many versions of the invention, this separation is between 2 and 6 mm.

Each tab 60 is generally in the form of a rectangle with rounded corners. Each tab 60 has a length (measurement along an axis parallel to the longitudinal axis of assembly 40) of between 0.5 to 5 mm. Often this length is between 2 and 4 mm. Each tab 60 has a width, (measurement along the axis perpendicular to the longitudinal axis of assembly 40 in the plane of FIG. 2) of 0.25 to 2 mm. In many versions of the invention, this width is between 0.5 to 1 mm. It should further be understood that each tab 60 attached to one bridge 54 or 56 is separate from the adjacent tab 60 attached to the adjacent bridge 56 or 58. The spacing between the adjacent tabs 60 extending from adjacent bridges is typically no more than 500 microns and preferably 100 microns or less. This small separation between adjacent tabs 60 reduces the amount of tissue that can grow between the tabs. If appreciable tissue were allowed to grow between the tabs 60, this tissue could inhibit later removal of the assembly 40.

Bridges 54, 56 and 58 are each shaped so that the width of the bridge between two longitudinally adjacent pairs of tabs 60 is greater than the width of the same bridge between the distally adjacent next pair of tabs. Thus, the width of each bridge between the first pair of tabs, the pair closest to drive module 44, and the adjacent pair of tabs is approximately 0.88 mm. The width of each bridge between the second and third pairs of tabs, (the pairs second and third closest to drive module 44) is approximately 0.80 mm. The width of each bridge between the eighth pair of tabs 60 and the adjacent ninth pair of tabs, the distal most pair of tabs 60 relative to drive module 44, is approximately 0.32 mm.

Beams 62 extend between the bridges 54, 56, and 58. More particularly, each beam 62 extends between adjacent bridges 54 and 56 or between adjacent bridges 56 and 58. In the illustrated version of the invention, assembly 40 is further constructed so that each beam 62 connecting bridges 54 and 56 is collinear with an adjacent beam connecting bridges 56 and 58. Each beam 62 has a width, (measurement along an axis parallel to the longitudinal axis of the assembly 40) of approximately 0.25 mm.

The electrode array 40 of FIG. 1 is further constructed so that there is a pair of collinear beams 62 adjacent the proximal and distal ends of each of the tabs 60 in each row of tabs. Thus, in the illustrated version of the invention, there are 18 pairs of beams that connected the spaced apart bridges 54, 56, and 58 together.

Given the spacing between the tabs 60, it should be appreciated that the longitudinally adjacent pairs of beams 60 are spaced apart from each other along the longitudinal axis of electrode array 40. As discussed below, a flexible membrane 64 is disposed between these adjacent spaced apart beams 62. In FIG. 2 membranes 64 are shown by surface shading. Similarly, there may also be membranes 66, located on the outer sides of bridges 54 and 58. Each of the membranes 66 extends between a pair of longitudinally adjacent tabs 60 that extend from the outer sides of bridges 54 and 58. Membranes 64 and 66 are present to inhibit tissue growth between the components of the electrode array 40.

Electrode array 40 is also formed to have a head 70 and two shoulders 78. Head 70 is located forward from a small neck 72 that forms the distal end of center-located bridge 56. Thus, neck 72 is located forward of the two distal most tabs 60 that extend outwardly from bridge 56. Each of the two distal most beams 62 extend from neck 72. Head 70 is located forward of the two distal most beams 62. Head 70 has a proximal edge that extends laterally beyond neck 72 on either side of the neck. The head 70 has two parallel side edges. At the most distal end, head 70 has an outwardly curved distally-directed front edge.

Each shoulder 78 extends forward from a small land 80 located forward of the associated outer bridge 50 or 54. Each land 80 is integral with and extends distally forward from the outer tab 60 integral with the bridge 54 or 58 with which the land is attached. Lands 80 serve as the terminuses for the beams 62 that extend from neck 72. Each shoulder 78 is spaced forward and away from the adjacent beam 62. Shoulders 78 are also spaced laterally away from the adjacent side edges of the head 72. Specifically, the shoulder 78 on the left side of FIG. 1 is spaced from the adjacent head side edge along a line collinear with the line along which the tabs 60 associated with bridge 54 are spaced from the adjacent tabs 60 associated with bridge 56. The shoulder 78 on the right side of FIG. 1 is spaced from the adjacent head side edge along a line collinear with the line along which the tabs associated with bridge 56 are spaced from the adjacent tabs 60 associated with bridge 58.

Each shoulder 78 is approximately in the shape of a right angle triangle wherein the 90° corner is located adjacent the bottom of the adjacent side of edge of the head 72. The hypotenuse edge of the shoulder 78 is the outer edge of the shoulder. Each shoulder 78 is, however, further shaped to have a rounded distal end 84. Beams 86 connect the hypotenuse of each shoulder 78 to the top of head 70.

An electrode 42 is disposed on each one of the tabs 60. Plural conductors 88 are disposed on bridges 54, 56 and 58. Each conductor 88 extends to a separate one of the electrodes 42 integral with the associated bridge 54, 56 or 58. In FIG. 1, due to scale, the set of conductors on each bridge is seen as a single black line. The thickness of this line decreases distally along the length of each bridge. This decrease in line thickness represents that, moving distally along each bridge 54, 56 or 58, the number of conductors present on the bridges decreases. Conductors 88 are the conductors over which current is sourced to or sunk from the electrodes 42. If an electrode 42 does not function as a current source or sink, the electrode may function as a voltage probe. When an electrode 42 performs this function, the associated conductor 88 serves as the conductor over which the sensed voltage is connected to a monitoring circuit (not illustrated and not part of this invention).

Each conductor 88 only extends as distally forward as the electrode 42 to which the conductor is connected. Each bridge 54, 56 and 58 therefore supports more conductors adjacent its proximal end than its distal end. This need to support the largest number of conductors adjacent the proximal ends of the bridges 54, 56 and 58 is why these ends of the bridges are wider than their complementary distal ends.

Figure 3:
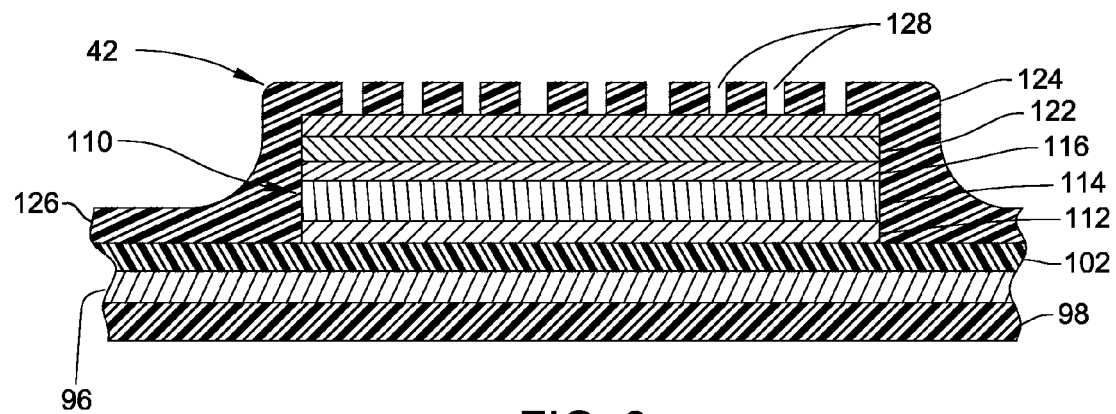
FIG. 3 is a cross sectional view across the length of a single electrode of the electrode array of FIG. 1.
Figure 4:
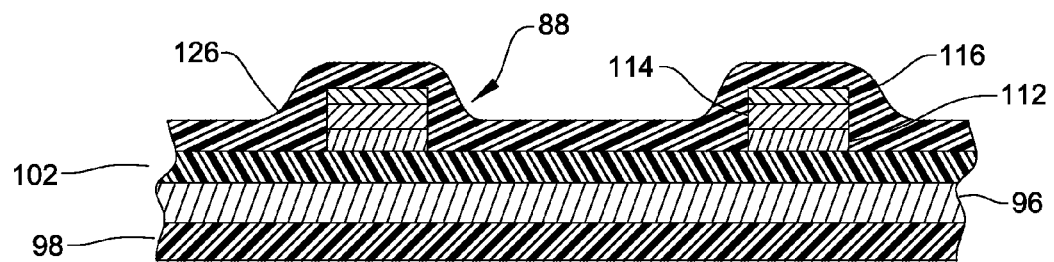
FIG. 4 is a cross sectional view across two conductors of the electrode array of FIG. 1.

Electrode array 40, as seen in FIGS. 3 and 4, has a frame 96 formed from a superelastic material; that is a material that, after being subjected to the strain induced by appreciable rolling, folding or bending, returns to its initial shape. In one version of the invention, the frame 96 is formed from a nickel titanium alloy such as Nitinol. Frame 96 is shaped to form the basic geometric features of the assembly including feet 53 and 57, legs 50 and 52, bridges 54, 56 and 58, tabs 60, beams 62 and 86, head 70, neck 72 shoulders 78 and lands 80. Terminal pad 46 and membranes 64 and 66 are formed from material different from which the frame 96 is formed.

Figure 5:
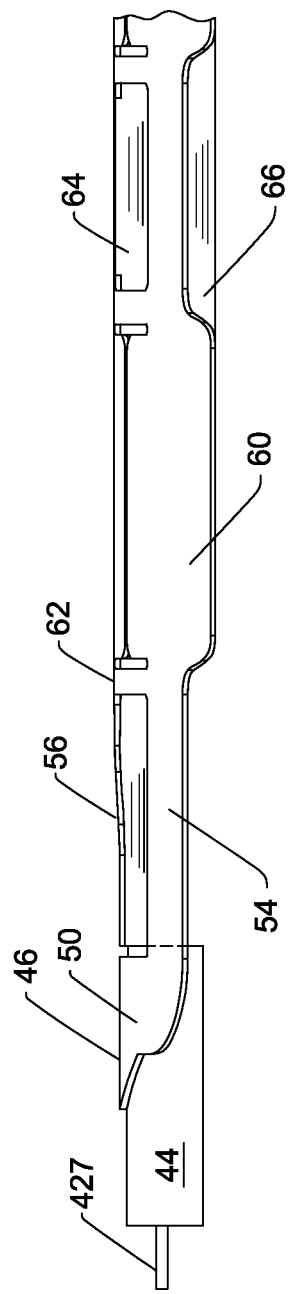
FIG. 5 is a side view of the proximal end of the electrode array showing how the assembly, when deployed, has a curved profile.

In some processes of manufacturing assembly 40, frame 96 is curved early in the manufacturing process. Specifically, the frame 96 is shaped to have a curvature intended to conform generally to the curvature of the surface of the tissue against which electrode array 40 is to be positioned. Often the arc of curvature is perpendicular to the longitudinal axis of the array 40. In these versions of the invention, when a manufactured assembly 40 is placed on a flat surface, with the electrodes 42 facing downwardly, center bridge 56 is elevated relative to side bridges 54 and 58 as seen in FIG. 5. More particularly, FIG. 5 illustrates the elevation of center bridge 56 relative to bridge 54.

Insulating material is disposed on the top, bottom and side surfaces of the frame 96 (side-located insulating material not shown). One such insulating material is a conformal coating such as the polyxylene polymer parylene-C. This insulating material is disposed over the surfaces of the frame 96. In FIGS. 3 and 4, the insulating material disposed over the surface of the frame 96 away from the tissue against which the assembly 40 is employed, is identified as passive side insulating layer 98. Passive side insulating layer 98, in addition to being disposed over the "passive" side of frame 96 is also disposed over the side edges of the frame.

The insulating layer disposed over the surface of the frame 96 on which electrodes 42 and conductors 88 is located is identified as the intermediate insulating layer 102. While not illustrated, it should be understood that the material forming intermediate insulating layer 102 also forms layers of terminal pad 46 and membranes 64 and 66.

Conductive traces that form base pads 110 of the electrodes 42 and the whole of the conductors 88 are disposed on the exposed surface of intermediate insulating layer 102. Typically, each conductive trace includes a thin layer of titanium 112 applied directly to intermediate insulating layer 102. A thicker layer of gold 114 is disposed over titanium layer 112. A thin outer layer of titanium 116 is disposed over the surface of the exposed surface of gold layer 114. Titanium layer 116 has a thickness approximately equal to that of titanium layer 112.

An electrode 42 of assembly 40 of this invention, in addition to having the titanium/gold/titanium base pad 110, has two additional layers deposited above the outermost titanium layer 116 of the base pad. While not clear from FIGS. 3 and 4, the gold layers 114 of electrodes 42 may be thicker than the gold layers 114 of conductors 88. As seen in FIG. 3, a second outer layer of titanium 122 is disposed over the outer surface of titanium layer 116. A layer of iridium 124 is disposed over the outer surface of the titanium layer 122. The exposed surface of the iridium functions as the tissue-contact face of the electrode 42.

An insulating layer, again possibly a polyxylene polymer coating, is disposed over at least a portion of each electrode 42 and over the whole of the conductors 88. This insulating layer is applied over the conductors 88 to prevent the conductors from functioning as electrodes. This insulating layer also functions as a laminate that adds structural strength to assembly 40. In the Figures, this insulating layer is identified as active side insulating layer 126. In some methods of manufacturing the electrode array 40, the material forming the active side insulating layer 126 is applied to cover the whole of the electrodes 42. Portions of this insulating material are removed to form small openings 128. Openings 128 are the openings through which the iridium layers 124 of the electrodes 42 are exposed to the target tissue.

The current driven between the array electrodes is applied to the drive module through a cable 132, seen in FIG. 1, attached to the proximal end of the drive module 44. Often the proximal end of the cable 132 is connected to an implantable device controller (IDC) 134 also implanted in the patient. Often the current sources and sinks are internal to the IDC 134. (The exact structure of the IDC is not relevant to this invention.) Typically, cable 132 contains plural individual conductors (not illustrated) that are connected to the various components internal to the drive module 44.

While not illustrated, it should be understood that cable 132 includes an insulating outer shell. The shell may be formed of material that can withstand some axial compressive loading without buckling. Cable 132 may also include an element connected to the electrode array 40 that can sustain axial tension. This allows cable 132 to be used as a extraction tether for removing the array 40.

A more detailed understanding of electrode array 40 as well as a description of one means for fabricating the array is contained in the incorporated by reference PCT Pub. No. WO 2009/111142 A2, and in U.S. Pat. Pub. No. US 2009/0293270 A1, METHOD OF ASSEMBLING AN ELECTRODE ARRAY THAT INCLUDES A PLASTICALLY DEFORAMBLE CARRIER also explicitly incorporated herein by reference.

II. Delivery Assembly

Figure 6:
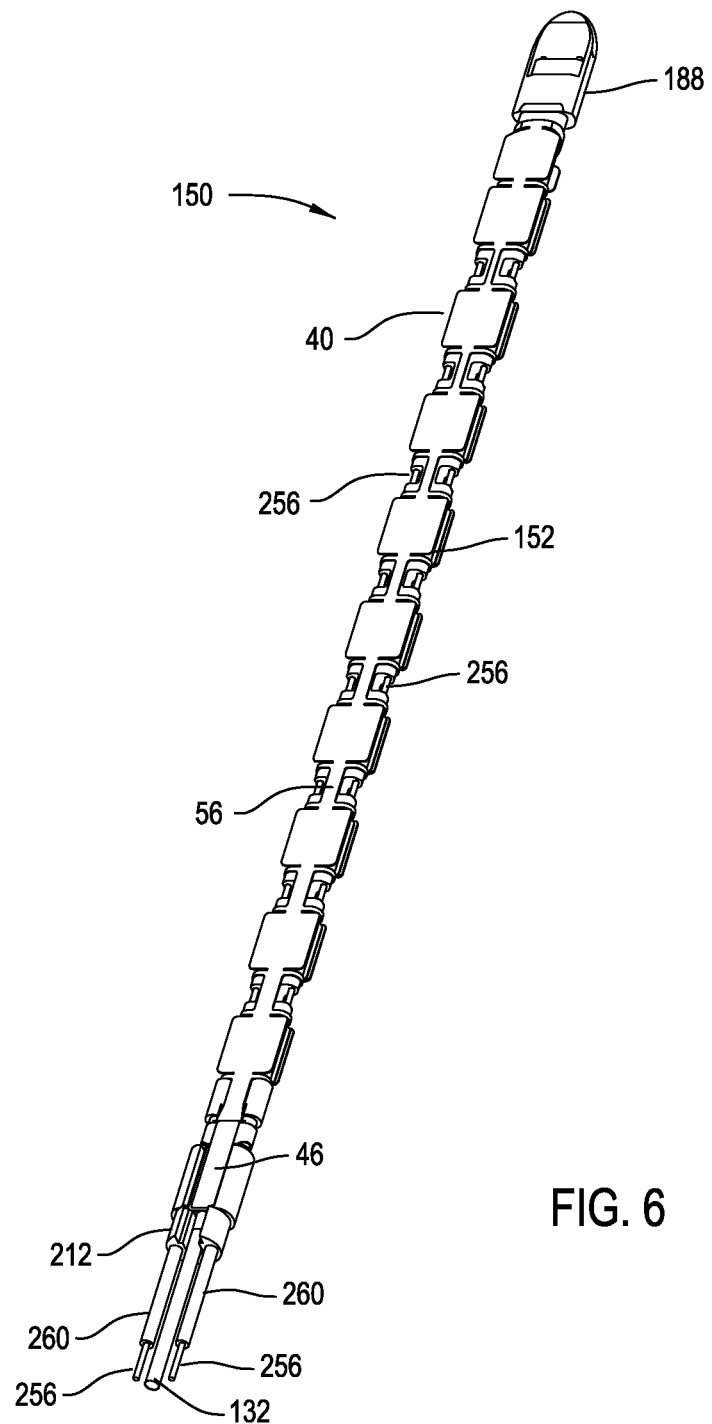
FIG. 6 is a perspective view of an electrode array wrapped around the steerable core of the delivery assembly of this invention.
Figure 7:
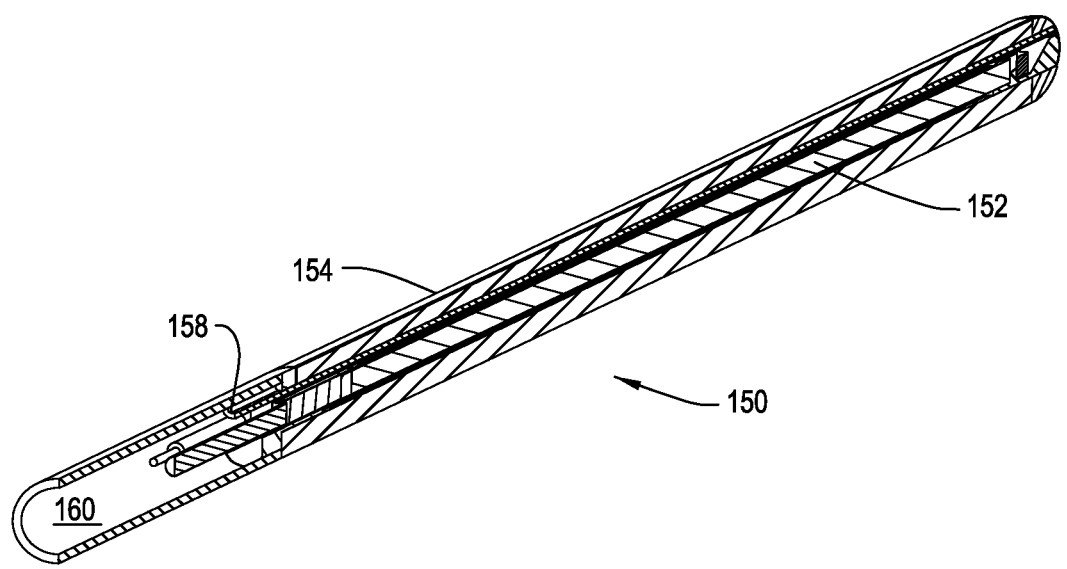
FIG. 7 is a perspective cross sectional view of an electrode array contained in the delivery assembly of this invention.

FIGS. 6 and 7 illustrate the delivery assembly 150 of this invention. Assembly 150 includes an elongated, flexible core 152. Electrode array 40 is wrapped, folded around core 152. The folded electrode array 40 and core 152 are encased in a sheath 154, also part of delivery assembly 150. Sheath 154 is opened, unrolled, along a slot 156 (FIG. 17) that extends longitudinally along the sheath. A retention bar 158, disposed inside sheath 154, above the folded over electrode array 40, holds the sheath closed.

Electrode array delivery assembly 150 also includes an elongated flexible, tube-like shaft 160. Core 152 and sheath 154 are located forward of the distal end of shaft 160. As discussed below, the deployment of array 40 concludes with the retraction of core 152, sheath 154 and shaft 160 away from the array.

Figure 8:
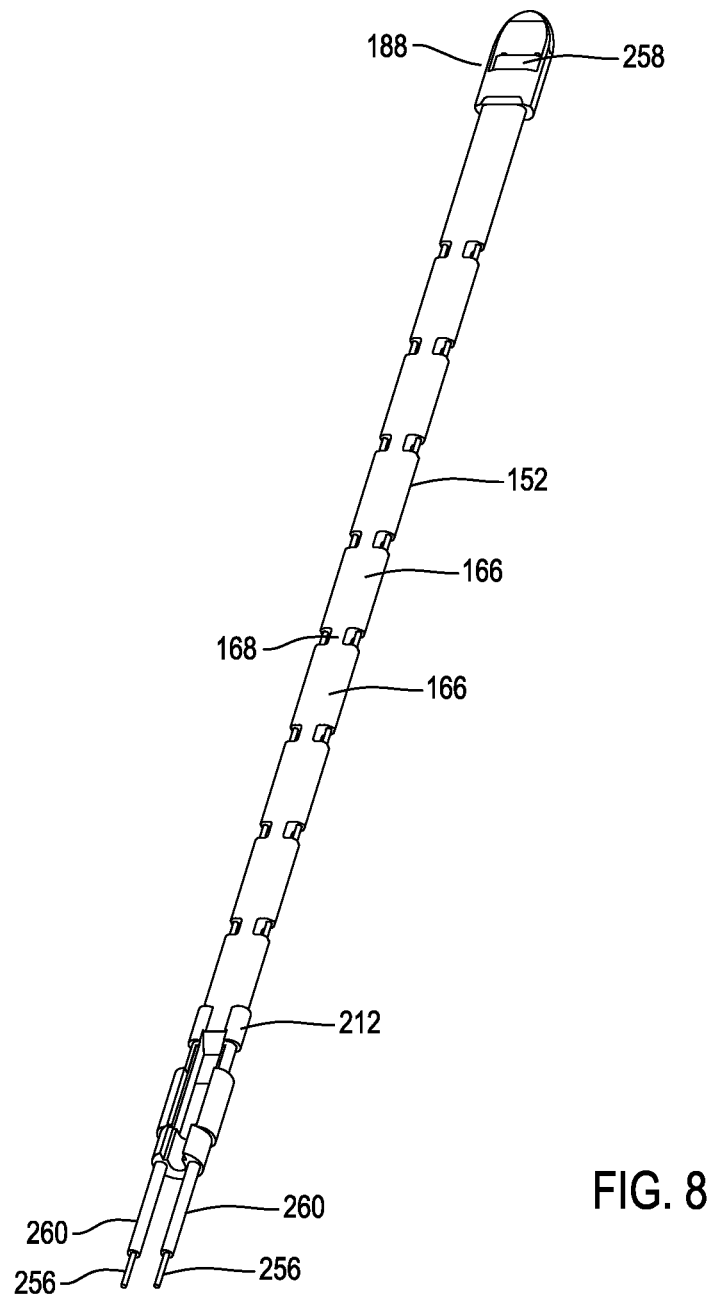
FIG. 8 is a perspective view of the core, anchors and steering cables of the delivery assembly of this invention.
Figure 9:
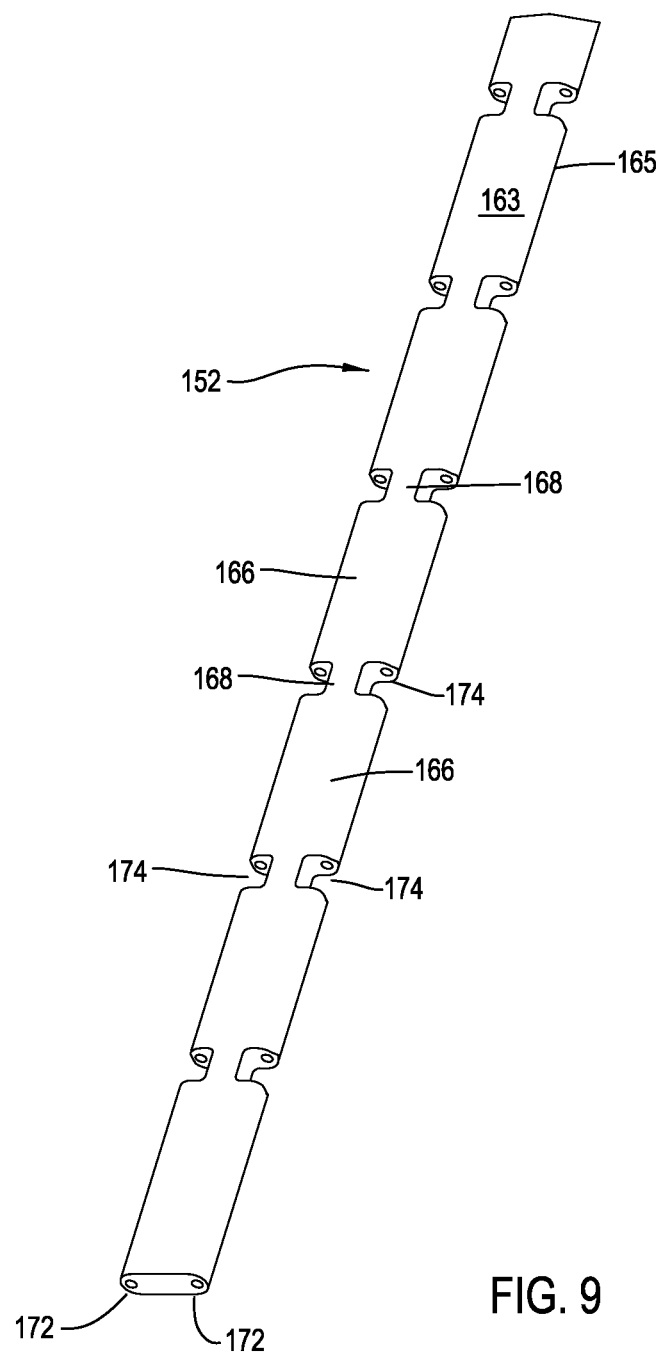
FIG. 9 is a perspective view of the proximal end of the core, with the rear anchor removed.

Core 152, now described with respect to FIGS. 8 and 9, is formed from a flexible biocompatible material such as a thermoplastic elastomer. In many versions of the invention, the material forming core 152 is also lubricious. Often the material forming core 152 has the cross section of a rectangle with opposed, semi-circular sides. Thus core 152 is shaped to have parallel, planar opposed top and bottom surfaces, only top surface 163 illustrated in FIGS. 8 and 9. Core 152 has a pair of semi-circular shaped side surfaces 165, only one of which is called out in FIG. 9. In some versions of the invention, the overall width of the core, the distance across the outermost sections of the of the adjacent opposed sides surfaces 165, is approximately 0.5 mm less than the outer side edge-to-outer side edge distance between a pair of opposed tabs 60 that extend from one of the bridges 54, 56 or 58 of electrode array 40. The arcuate length around each core side surface 165 is less than the length of the array beams 62 that are wrapped around the side surfaces. The radius of curvature of core side surfaces 165 is such that, when a beam 62 is wrapped around a surface 165, the beam will not be curved so tightly that the beam will undergo plastic deformation. The minimal thickness of core 152, from the top surface to the opposed bottom surface is a function of the maximum allowable strain supportable by the array frame 96 before plastic deformation. This strain is inversely related to the thickness of the frame 96.

The core 152 is further formed to have two parallel bores 172 that extend longitudinally through the core. Each bore 172 is centered around a separate one of the axes internal to the core 152 around which a separate one of the side surfaces 165 is curved. Core 152 is further formed so as to have a number of notches 174 that extend inwardly from the side surfaces 165. Each notch 174 is approximately 0.1 to 1.5 mm in length and 0.7 to 1.0 mm in depth. (Here "length" is the dimension parallel to longitudinal axis of core 152; "depth" is the dimension inward from the side surface 165.) The depth of the notches 174 is such that they intersect bores 172. Notches 174 are arranged in coplanar pairs such that where a notch extends inwardly from one side surface 165 a notch extends inwardly from the opposed side surface 165.

Notches 174 divide core 152 into a set of connected, longitudinally aligned islands 166. A link 168 connects two adjacent islands 166. Each link 168 is the portion of the core 152 between two side-by-side notches 174. Islands 166 are thus wider, (the dimension perpendicular to the longitudinal axis of the core 152) than the links 168. Each island 166 typically has a length (the dimension along the longitudinal axis of the core 152) that is at least equal to if not greater than the length subtended by an array beam 62, the tab 60 closest to the beam 62, the beam 62 on the opposed sides of the tab and the gaps between the tab and the beams. Thus in one version of the invention if the distance between the proximal end of beam 62a of FIG. 2 and the distal end of beam 62b of the same Figure is 4.0 mm, core 152 may have islands 166 with a length that is between 4.0 and 5.5 mm.

A front anchor 188 is disposed over the distal end of core 152. A rear anchor 212 is disposed over the proximal end of the core 152.

Figure 10:
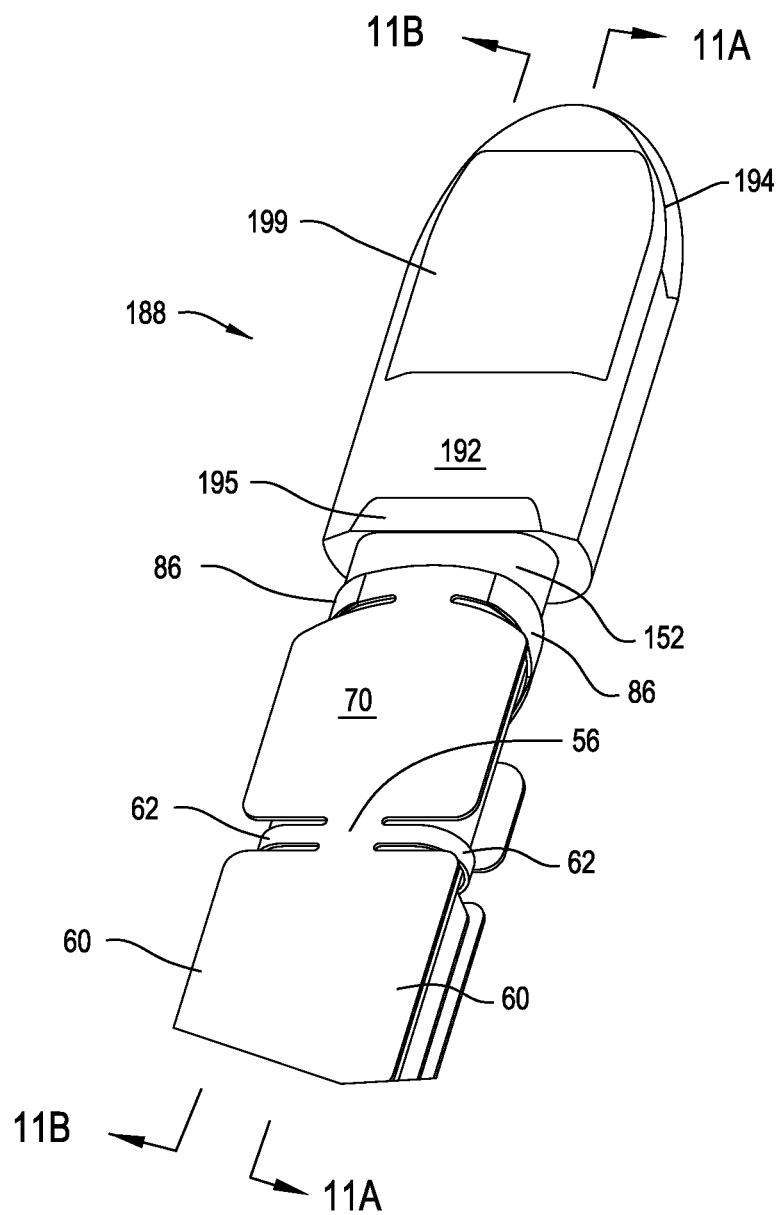
FIG. 10 is a perspective view of the distal end of the core and the front anchor wherein the electrode array is shown wrapped around the core.
Figure 11A:
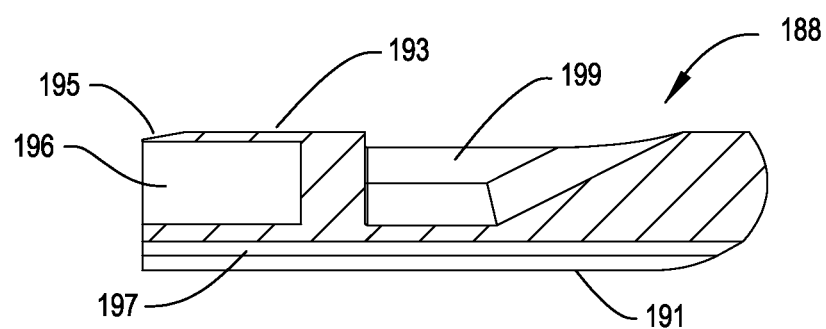
FIG. 11A is a cross sectional view of the front anchor of FIG. 10, taken along line 11A-11A wherein the core and electrode array are removed.
Figure 11B:
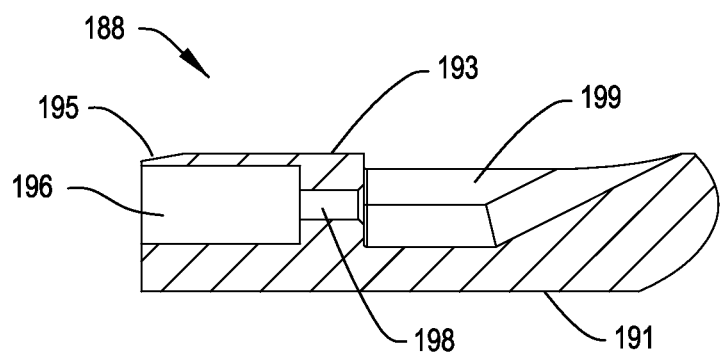
FIG. 11B is a cross sectional view of the front anchor of FIG. 10, taken along line 11B-11B wherein the core and electrode array are removed.

The front anchor 188, now described by reference to FIGS. 10, 11A and 11B, is formed from a relatively rigid biocompatible polymer such as a thermoplastic. Front anchor 188 is formed to have a base 192 with an oval cross sectional shape. The top-to-bottom height and side-to-side width of anchor base 192 are greater in size than the corresponding dimensions of the adjacent core 152. Forward of base 192, the front anchor 188 has a head 194. Head 194, when viewed from above, the view of FIG. 10, has a rounded shape. Thus, the side-to-side width of front anchor head 194 decreases distally from anchor base 192. In the Figures, it can be seen that the front anchor has a bottom surface 191 that extends the length of base 192 and to almost the distal end of the head 194. Anchor bottom surface 191 is generally planar. However, as seen by reference to FIG. 11A, front anchor is formed to have groove 197 that extends upwardly from the bottom surface 191. Groove 197 is centered along the longitudinal axis of the front anchor 188. Front anchor 188 has a top surface 193 that is parallel to bottom surface 191 on the opposed face of the anchor 188. The portion of the top surface 193 parallel to bottom surface 191 extends from the anchor head 194 to close to the proximal end of the anchor base 192. At the most proximal end of the top face of front anchor 188 there is a ramp surface 195. Ramp surface 195 inclines upwardly from the proximal end of the front anchor 188 to the abutting top surface 193.

Front anchor 188 is further formed to have a pocket 196 that extends forward from the proximal end of anchor base 192. Pocket 196 is dimensioned to closely receive the distal end of the adjacent core 152. Front anchor 188 is further formed so as to have a recess 199 that extends inwardly from top surface 193. More specifically, the anchor 188 is formed so that, rearward of the head 194, recess 199 tapers inwards from the distal end of the anchor top surface 193 towards the opposed bottom surface 191. At a location along the length of the anchor 188 slightly proximal to where the anchor base 192 transitions into the anchor head 194, the base of the recess bottoms out. In the illustrated version of the invention, this planar base of recess 199 is slightly below the surface internal to anchor base 192 that defines the bottom surface of pocket 196.

Two parallel bores 198 extend longitudinally through anchor 188. (One bore 198 shown in cross section in FIG. 11B.) Each bore 198 extends from the distal end of pocket 196 to the surface that defines the proximal end base of recess 199. Anchor 188 is formed so that when core 152 is seated in pocket 196, anchor bores 198 are concentric with core bores 172.

Figure 12:
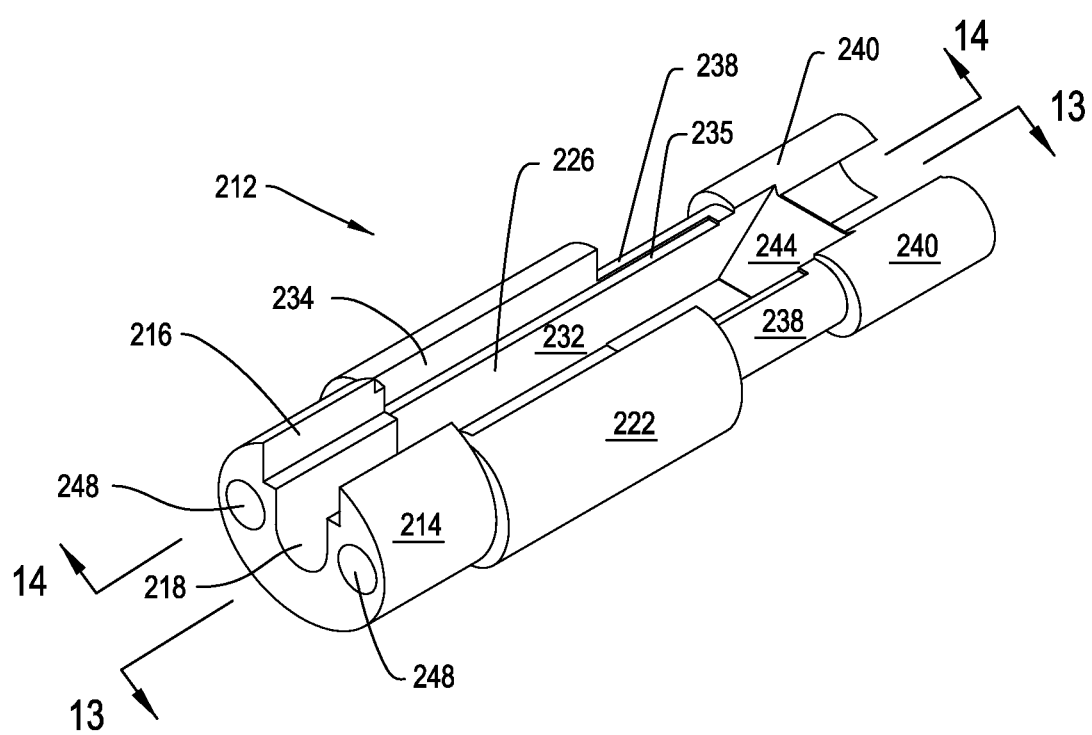
FIG. 12 is a perspective view of the rear of the rear anchor.
Figure 13:
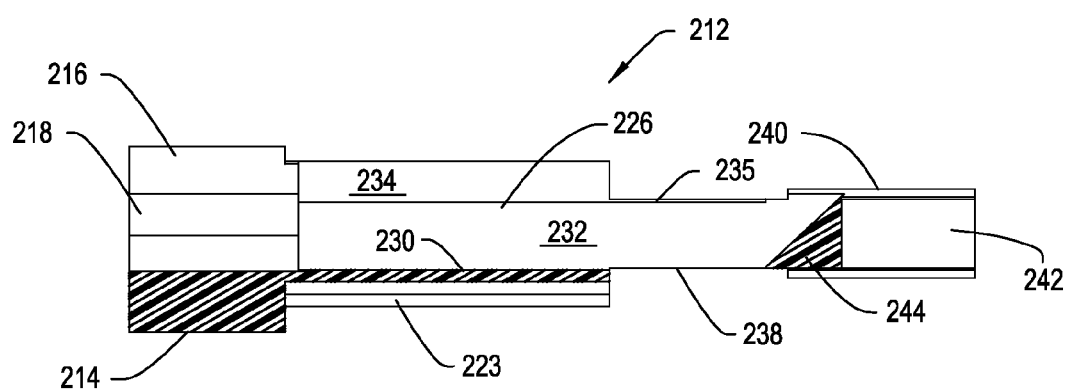
FIG. 13 is a cross sectional view of the rear anchor taken along line 13-13 of FIG. 12.
Figure 14:
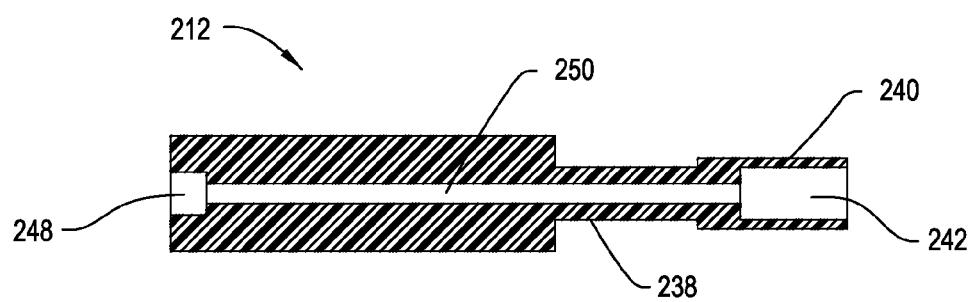
FIG. 14 is a cross sectional view of the rear anchor taken along line 14-14 of FIG. 12.

Rear anchor 212, seen best in FIGS. 12-14, is fitted over the proximal rear end of the core 152. Rear anchor 212 includes a tail 214 that forms the proximal rear end of the anchor. Tail 214 has an elliptical shape. The tail 214 is further formed to have in the top surface, (surface not identified) two longitudinally extending grooves that project downwardly. Close to the tail top surface there is a top groove 216. Rear anchor 212 is shaped so that top groove 216, when looking towards the proximal end of the anchor 212, has a rectangular cross sectional profile. A bottom groove 218 extends downwardly from the base of top groove 216. Groove 218 is U-shaped. Groove 218 is dimensioned to receive power cable 132. In the illustrated version of the invention, the side-to-side width of bottom groove 218 is less than the corresponding width of top groove 216.

Forward of and integral with tail 214, rear anchor 212 is formed to have a torso 222. Torso 222, like tail 214, is elliptically shaped. In the illustrated version of the invention, the longitudinal axes of tail 214 and torso 222 are in registration. The torso 222 is shaped to have a longer side-to-side width than tail 214 and shorter top-to-bottom height. Consequently, the top and bottom surface of the tail 214 are located, respectively, above and below the adjacent surfaces of the torso 222. The sides of the torso 222 extend beyond the sides of the tail 214

Torso 222 is further formed so as to have a groove 223 that extends inwardly from the torso bottom surface. Groove 223 extends longitudinally along the length of the torso and is located below the longitudinal axis of rear anchor 212. Groove 223 has a concave cross sectional profile.

Anchor torso 222 is further formed to define a void space 226 that extends inwardly from the top surface of the torso. (Arbitrarily the "top surface" of torso 222 is the side visible in FIG. 12. The "bottom surface" of the torso is the side opposite from top side.) Torso void space 226 extends longitudinally along the whole of the length of the torso 222. Void space 226 is contiguous with tail grooves 216 and 218. The base of void space 226 is defined by a bottom panel 230 that is part of the torso 222. Bottom panel 230 is located below the base of tail bottom groove 218 so as to provide void space 226 with a depth greater than that of groove 218. Two sets of opposed side walls 232 and 234, also part of the torso 222, define the lateral sides of void space 226. A first pair of side walls, walls 232, (one shown) extends upwardly from the opposed longitudinally extending sides of bottom panel 230. Side walls 232 are spaced apart a distance that is slightly greater than the width of electrode array drive module 44. Rear anchor 212 is further shaped so that side walls have 232 have a height approximately equal to that of drive module 44. The second set of side walls, walls 234, (one shown) extend above walls 232 to the top of anchor torso 222. Walls 234 are parallel with walls 232. Each wall 234 is stepped outwardly relative to the adjacent wall 232. Walls 234 are thus spaced apart from each other by a distance greater than the width of any portion of the electrode array terminal pad 46 that may be seated in the torso 222.

Extending distally forward from torso 222, rear anchor 212 is formed to have two parallel, forward extending, spaced apart arms 238. Each arm 238 is in the shaped of a filled-in "D" wherein the curved sections of the arms are outwardly directed. Arms 238 are spaced apart a distance equal to the width of torso void space 226. The distance across the arms 238, from outermost surface to outermost surface, is equal to the width across core 152. The radius of curvature around the outer surfaces of the arms 238 is equal to the radius of curvature around core side surface 165. Anchor arms 238 are further formed to each have a step 235 that extends inwardly from the top surface of the arm, (one step seen in FIGS. 12 and 14). Each step 235 is coplanar with the adjacent step in the anchor torso 222 between walls 232 and 234 (torso step not identified). Steps 235 do not extend the complete length of each arm 238. Instead, each step 235 extends distally forward from the torso approximately five-sixths the length of the arm 238.

A finger 240 extends forward from each arm 238. Each finger 240 is "C"-shaped wherein the curved surfaces of the fingers 240, like the curved surfaces of arms 238, are outwardly directed. Fingers 240 are further formed to have a radius of curvature greater than the radius of curvature of arms 238. The outer surfaces of fingers 240 thus extend beyond the outer surfaces of the adjacent arms. Each finger 240 is further formed to have a U-shaped groove 242. Each groove 242 is positioned so that the curved base of the groove is outwardly directed towards the opposed finger 24. Grooves 242 extend longitudinally rearward from the distal front end of the fingers 236. Grooves 242 do not, however, extend the full length of the fingers 240. Each groove stops at a position located approximately three-quarters the distance from the distal end of the finger 240 towards the proximal end of the finger. Collectively, the fingers 240 are formed so that a side portion of the proximal end of core 152 can seat in each one of the grooves 242.

Rear anchor 212 is further formed to have a wedge 244 that extends between the opposed arms 238 and fingers 244. Wedge 244 is generally in the shape of solid right angle triangle. Wedge 244 is oriented so the inclined surface of the wedge angles upwardly from the proximal end of the wedge to the distal end. Also, the forwardly directed distal face of the wedge 244 is flush with surfaces internal to fingers 240 to function as the bases of grooves 242. Wedge 244 is further shaped so that proximal edge leading to the inclined surface is at an elevation equal to or slightly below the planar face of panel 230 that defines the base of the torso void space 226.

Two parallel, spaced apart bores 250 (one seen in the cross sectional view of FIG. 14) extend longitudinally through rear anchor 212. Each bore 250 starts at the proximal end of the anchor tail 214, extends forward through the torso 222 and one of the arms 234. Each bore 250 extends through the finger 240 associated with the arm 234 through which the bore extends and opens into the internal face of the finger that defines the groove 242 integral with the finger. Bores 250 are located so that when the rear anchor 212 is fitted to core 152, the bores 250 are in registration with core bores 172. The proximal end of the anchor tail 214 is further formed to have two counterbores 248. Each counterbore 248 is concentric with and opens into a separate one of the bores 250.

In some versions of the electrode array delivery assembly 150 of this invention, front and rear anchors 188 and 212, respectively, are molded in place over, respectively, the distal and proximal ends of core 152. Alternatively, after anchors 188 and 212 are fabricated, core 152 is molded into the anchors.

Delivery assembly 150 also includes a pair of steering cables 256, now described by reference to FIGS. 8, 15 and 16. Steering cables 256 are formed from materials having a high modulus of elasticity such as stainless steel or arimid fiber. Each steering cable 256 extends from a location proximal to assembly 150 into one of the rear anchor counterbores 248 and complementary bores 250. From the rear anchor bore 250, the steering cable 256 extends through the adjacent core bore 172. Each steering cable 256 therefore extends through the notches 174 in the core 152 that intersect the core bore 172 in which the cable is disposed. Steering cables 256 extend out of the core bores 172 into and through the complementary front anchor bores 198.

An oval-shaped bar 258 seated in front anchor recess 199 holds the distal ends of the steering cables 256 in the recess. Bar 258 has two spaced apart through holes (not illustrated) that are the same distance apart as anchor bores 198. Each steering cable 256 is tightly secured in a separate one of the bar bores. In some versions of the invention, the bar 258 is crimped inwardly to hold the cable in place. Alternatively the cable may be solder or adhesively secured to bar 258.

Each steering cable 256 extends rearwardly away from the rear anchor 212. Proximal to the rear anchor 212, each cable 252 is slidably disposed in a separate cable sheath 260. The distal ends of cable sheaths 260 are seated in separate counterbores 248 integral with the rear anchor 212. Cable sheaths 260 are formed from a low friction material that is relatively stiff in the axial direction such as a PTFE, polyethylene or stainless steel. In FIGS. 6 and 8, cable sheaths 260 are only shown extending a relatively short distance rearward of rear anchor 212. In practice, cable sheaths 260 extend rearward so as to cover substantially all of the portions of the steering cables 252 that extend rearward from anchor 212.

Figure 17:
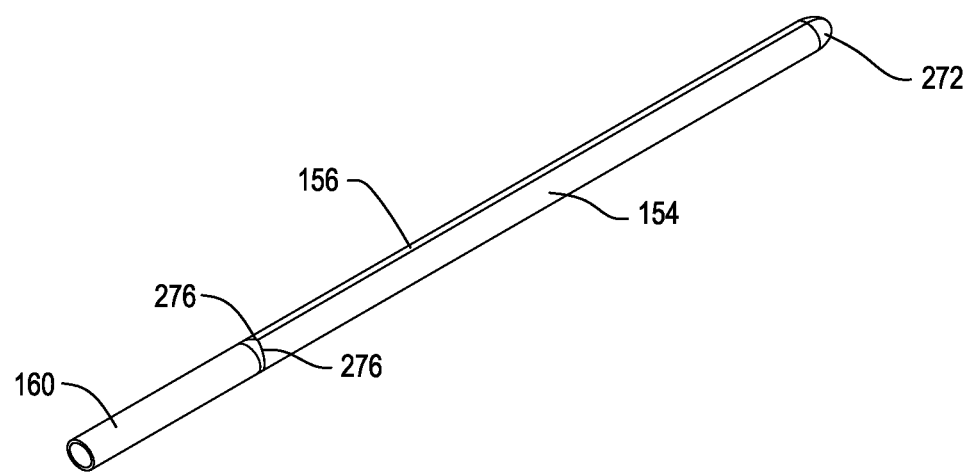
FIG. 17 is a perspective view of the delivery assembly sheath in the closed state.
Figure 18:
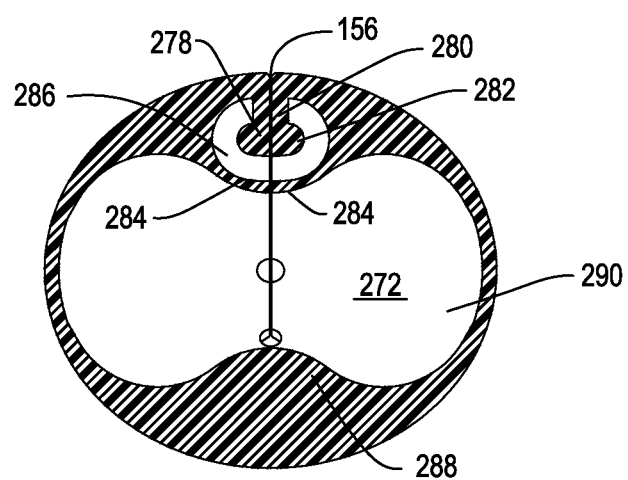
FIG. 18 is a cross sectional view of the sheath of FIG. 17 along line 18-18 of FIG. 17 wherein for purposes of clarity, no components are disposed in the sheath.

Turning to FIGS. 17 and 18, the structure of the assembly sheath 154 is now described. Sheath 154 is formed from a flexible, lubricious low-durometer material (less than 40 A Scale) such as a silicone rubber. In cross section, along a plane perpendicular to the longitudinal axis of the sheath 154, the sheath 154 is shaped to, when folded, has an elliptical outer profile. The sheath 154 is further formed to have a front end with a rounded head 272. The assembly sheath 154 is further formed to have a slit 156 that extends longitudinally along the length of the sheath. Slit 156 extends approximately 100° degrees around the outer surface of the sheath head 272 so as to intersect the most distal portion of the head. The slit 156 then extends rearward towards the proximal end of the sheath 154. Slit 156 does not extend the length of the assembly sheath 154. Instead, the slit 156 terminates at location approximately 5 mm forward of the proximal end of the sheath. Two side slits 276 angle away from opposed sides of the longitudinally extending slit 156. Each side slit 276 angles away from the longitudinally extending slit 156 by approximately 120°. Each side slit 276 subtends an angle of approximately 100° around the circumference of the sleeve.

Assembly sheath 154 is further formed to have two symmetrically arranged, longitudinally aligned ribs 278. Each rib 278 extends inwardly from one of the opposed edges of the sheath 154 that defines slit 156. Each rib 278 has a stem 280 and a head 282. On the outer side of each rib 278, stem 280 and head 282 share a coplanar side surface, (surface not identified). On the opposed side of the rib 278, the head 282 curves outwardly away from the stem. As seen in FIG. 18, when the ribs 278 are pressed together planar side-to-planar side, the ribs 278 collectively have a cross sectional shape similar to that of an inverted mushroom.

Sheath 154 is further shaped to have a pair of flaps 284. Each flap 284 extends outwardly from an inner surface of the sheath adjacent one of the ribs 278 and extends over the adjacent rib. Each flap 284 is typically spaced away from the associated rib 278 so as to form a channel 286 between each rib and the associated flap. When sheath slit 156 is closed, channels 286 are contiguous with each other. Ribs 278 and flaps 284 are collectively formed so that when the sides of sheath 154 are place together, the abutting channels 286 collectively have a C-shaped cross sectional profile.

The assembly sheath 154 is further shaped so as to have an internal longitudinally extending rib 288. Rib 288 extends upwardly from the inner surface of sheath 154. More particularly, sheath 154 is formed so that when the sheath is in the closed state, slit 156 and rib 288 are diametrically opposed from each other. It should likewise be understood that when sheath 154 is in the closed state, the sheath defines a lumen 290 that generally has a Figure-8 cross sectional shape. Sheath 154 is formed so that that width across lumen 290, the width along the horizontal axis of FIG. 18, is less than the width across electrode array 40 when the assembly is in the unfolded, deployed, state. The width across lumen 290 is, however, equal to or slightly greater than the width of electrode array 40 when the assembly is in the folded state. This width is inherently greater than the side-to-side surface width across the core 152. The height of lumen 290, the vertical height in FIG. 18, varies along the width of the lumen. The height is a minimum between the abutting flaps 284 and the apex of rib 288.

Figure 19:
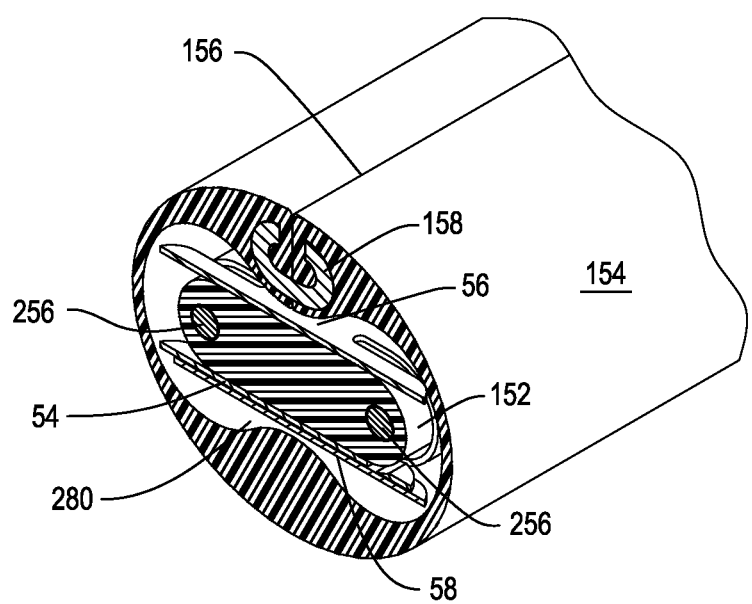
FIG. 19 is a is perspective cross sectional view of the delivery assembly of this invention showing the electrode array and core encased in the sheath.

Retention bar 158, seen best in FIGS. 7 and 19, is formed from a stainless steel or other low stretch material. Retention bar 158 is shaped so as to fit inside the abutting channels 286 internal to sheath 154. Thus, in the illustrated version of the invention, retention bar 158 has a C-shaped cross sectional profile. Retention bar 158 has a distal end located adjacent to the distal ends of the sheath abutting channels 286. Retention bar 158 extends out the proximal end of sheath 154, over rear anchor 212 and into flexible shaft 160. In some versions of the invention, the retention bar 158 extends out the open proximal end of shaft 160. In other versions of the invention, the retention bar 158 terminates in the flexible shaft 160. In these latter versions of the invention, a tether (not illustrated) extends proximally from the proximal end of the retention bar 158. The tether extends through the flexible shaft 160.

Returning to FIGS. 6, 7 and 10, it can be appreciated that a first step of preparing electrode array 40 for insertion and deployment is to wrap the assembly around core 152. This process is performed by centering the assembly 40 so that bridge 56 is disposed over core top surface 163. More specifically bridge 56 is positioned so that each electrode-carrying tab 60 integral with bridge 56, as well as the opposed assembly beams 62 adjacent the proximal and distal ends of the tab, are centered over one of the core islands 166. During the bending process, the beams 62 may curve around the adjacent core side surfaces 165. Owing to the relative dimensioning of the array 40 and the core 152, this curving is not so great that it results in plastic deformation of the beams 62. Again, it should be understood that each core island 166 is often slightly longer in length than electrode array tabs 60 and adjacent beams 62 that overlie the island.

A large section of each tab-free and bridge-free section of bridge 56 is disposed over one of the island-connecting links 168.

Figure 15:
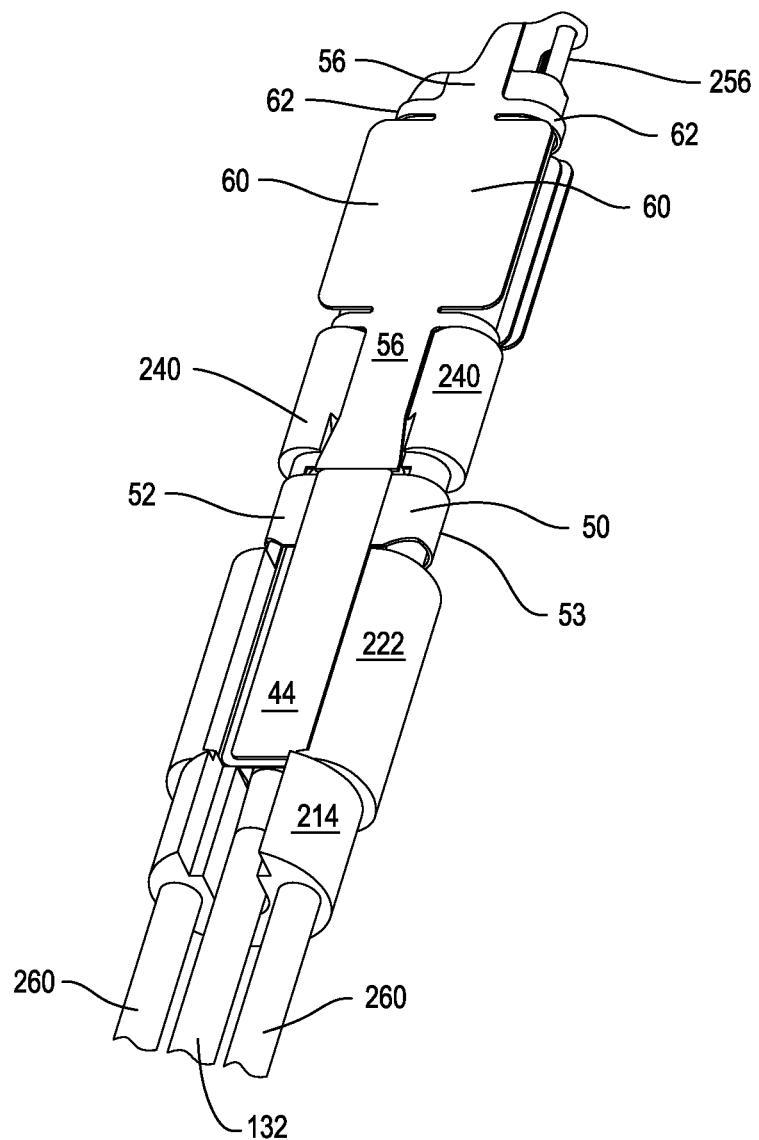
FIG. 15 is an enlarged perspective view of the proximal end of the core and rear anchor with the electrode array disposed around the core and rear anchor.

During the process of positioning electrode array bridge 56 over core 152, drive module 44 is seated in the rear anchor void space 226 as seen in FIG. 15. As a result of the drive module 44 seating in the anchor void space 226, any perimeter portions of the assembly terminal pad 46 that extend beyond the drive module seat in the stepped space between anchor walls 232 and 234 and step 235. Cable 132, which extends rearward from the drive module 44, is disposed in anchor grooves 216 and 218.

Once the drive module 44 and bridge 56 of assembly 40 are properly positioned, the assembly frame 96 is folded or bent to wrap bridges 54 and 58 around the opposed under-surface of the core 152, the surface opposite the core surface against which bridge 56 is disposed as seen in FIG. 19. Electrode array 40 may be folded so that either bridge 54 or bridge 58 is disposed against core 152; the other of bridge 58 or bridge 54 is disposed against the bridge immediately adjacent core 40. Since the electrode-carrying tabs 60 of bridges 54, 56 and 58 are laterally aligned, it should be appreciated that each tab 60 integral with bridge 54 or 58 is disposed against the rear surface of one of the core islands 166. Again, the beams 62 immediately adjacent the proximal and distal ends of each tab 60 are bent around the island 166 against which the tab is disposed. As a consequence of this folding or bending of the electrode array 40 around the core 152, as seen in FIGS. 6 and 15, portions of the assembly feet 53 and 57 and legs 50 and 52 are wrapped around the outer curved surfaces of arms 234 of rear anchor 212.

Figure 16:
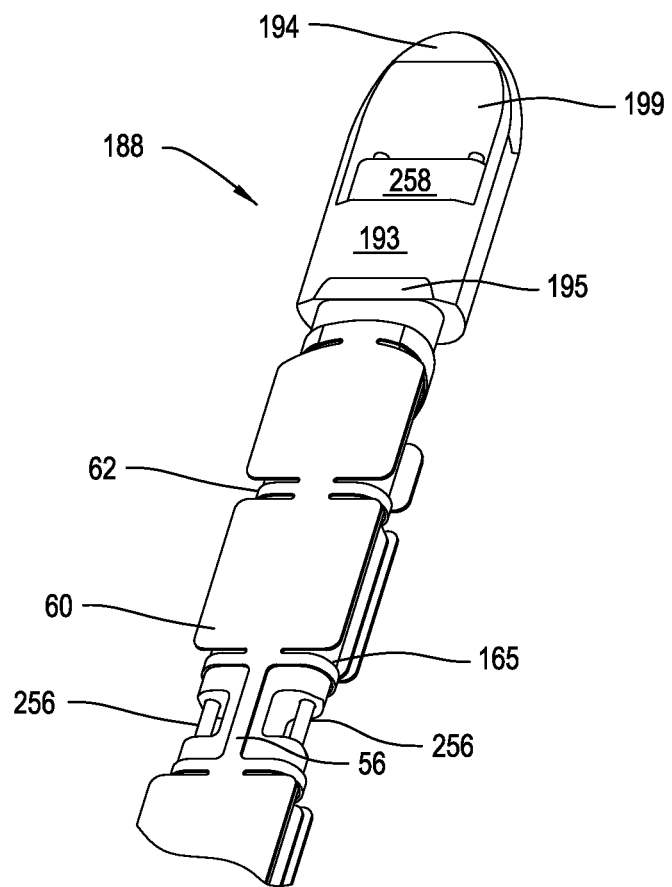
FIG. 16 is an enlarged perspective view of the distal end of the core and front anchor with the electrode array disposed around the core.

Collectively the components of this invention are further dimensioned so that, as seen in FIG. 16, assembly head 70, shoulders 78 and the top most tabs 60 closes the head are disposed over the distal most core island 166.

Once the electrode array 40 is wrapped or folded over core 152, sheath 154 is wrapped over the assembly 40 and core 152. To facilitate the proper orientation of components, core 152 is positioned over the unwrapped sheath 154 so that sheath rib 288 seats in front anchor groove 197 and rear anchor groove 223. Sheath 154 is then wrapped over the electrode array 40 and core 152. Retention bar 158 is then inserted in sheath channels 286 to hold the sheath 154 in the closed, folded, state. As seen by reference to FIG. 19, when assembly 40 and core 152 are disposed in sheath 154, the components of this invention are dimensioned so that the outer surfaces of flaps 284 press against the adjacent surface of bridge 56. The outer surface of rib 288 presses against the surface of the adjacent bridge 54 or 58. The compression forces flaps 284 and rib 288 place on the folded over assembly 50 hold the assembly, and also core 152, in a fixed orientation within sheath 154.

When sheath 154 is disposed over the electrode array 40, membranes 66 inhibit the outermost tabs 42 from cutting into the sheath.

Figure 20:
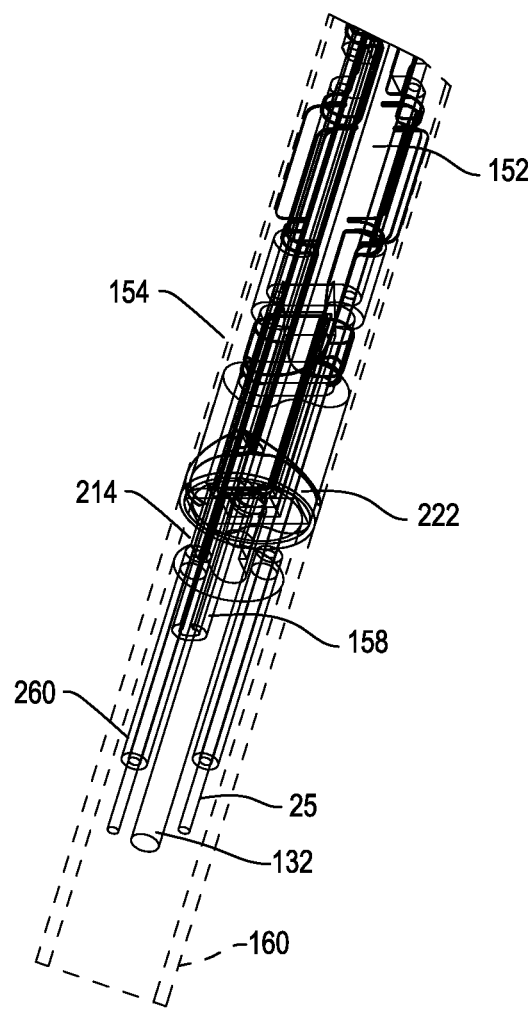
FIG. 20 is a perspective view of a how the proximal end of the electrode array, core and rear anchor are encased in the sheath.
Figure 21:
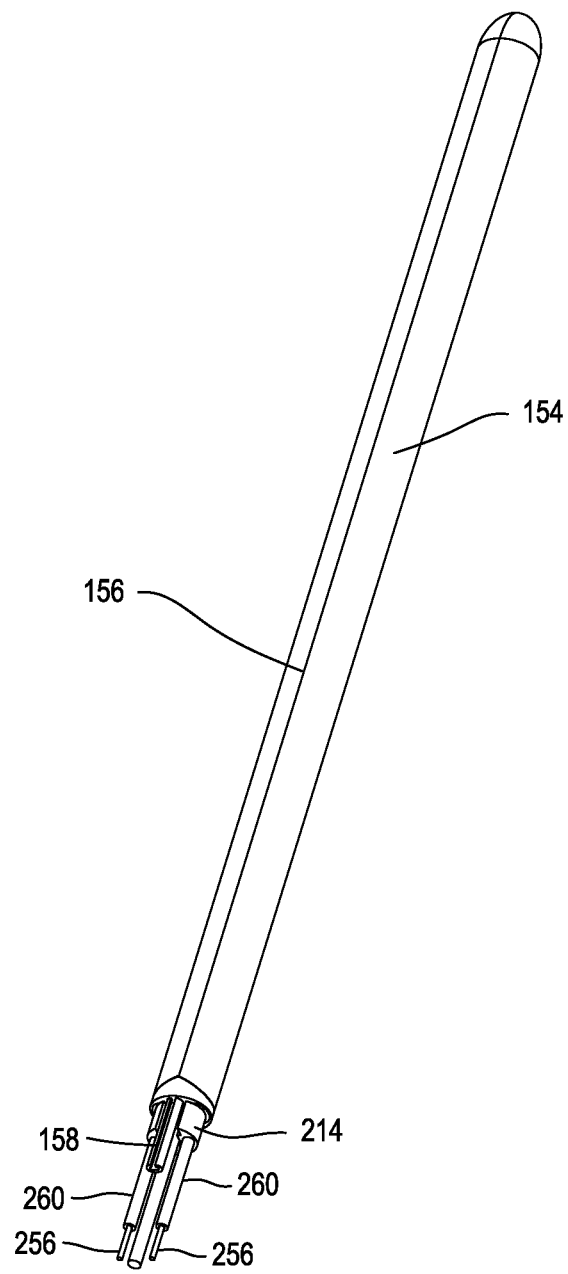
FIG. 21 is a perspective view of the components that extend out of the sheath.

As seen in FIGS. 7, 20 and 21, when assembly 40 and core 152 are in sheath 154, the sheath also encloses most but not all of rear anchor 212. In FIG. 20, to simplify illustration of the relationship between the components of this invention, sheath 154 and shaft 160 are represented by dashed lines. Specifically, the proximal end of sheath 154 is wrapped over the rear anchor torso 222. Rear anchor tail 214 extends rearwardly out of the sheath 154. Extending beyond the rear anchor tail are: cable 132; retention bar 158; and the sheath-encased steering cables 256.

The shaft 160 is generally in the form of a tube. The material forming shaft 160, while bendable, can withstand some axial loading without buckling. Shaft 160 can be fabricated from a polyurethane plastic. Shaft 160 covers rear anchor tail 214 and the components that extend rearwardly from the tail. This is represented by FIG. 21 wherein the position of rear anchor 212 relative to sheath 154 is shown. In some methods of preparing this invention for use, the rear anchor 212 is fitted in the open distal end of the shaft 160. The other components are then threaded through the shaft prior to encasing the electrode array wrapped core in sheath 154. In other versions of preparing the invention for use, after the electrode array wrapped core 152 is encased in sheath 154, shaft 160 is slipped over cable 132, retention bar 158 and steering cables 256. The distal end of shaft 160 is fitted over rear anchor tail 214. In either method of assembly, rear anchor 212 is attached to shaft 160 to move with the shaft. The proximal end of sheath 154, the portion located proximal to slits 156 and 276, is attached to the rear anchor 212.

III. Insertion and Deployment

Figure 22:
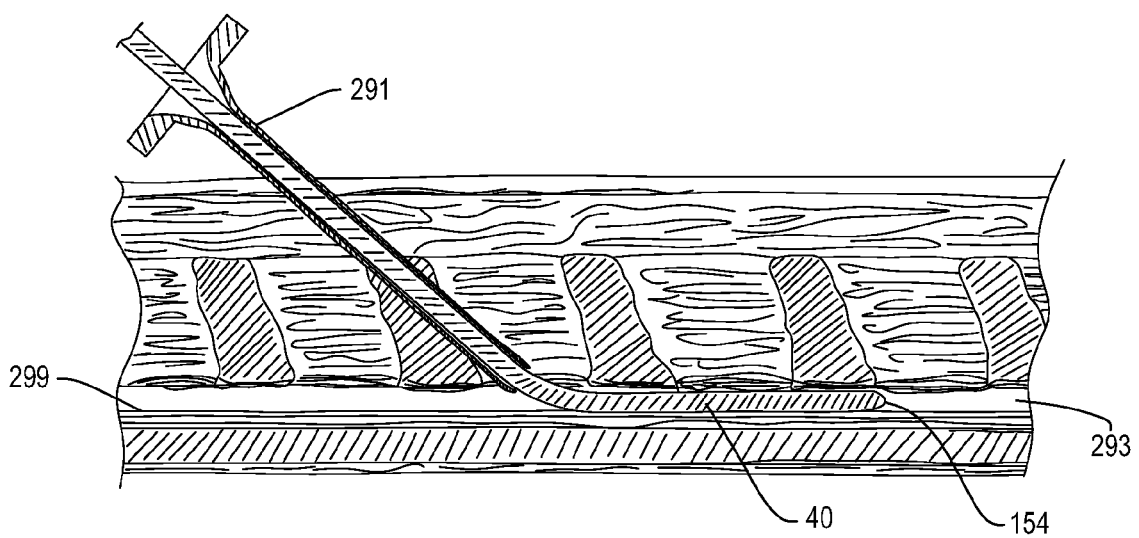
FIG. 22 is a cross sectional view of how an access cannula is used in one method to facilitate the deployment of an electrode array according to this invention.

Delivery and deployment of electrode array 40 of this invention starts with the insertion of an access cannula into the patient. The cannula is directed to a location, medically "a potential space," contiguous to where the array 40 is to be deployed. Often, a needle and a stylet disposed within the needle are employed to establish a path to a targeted potential space. This path is enlarged with dilators. Alternatively, a guide wire is threaded along this path. The guide wire provides guidance for the subsequent insertion of the access cannula along the path. In FIG. 22, an access cannula 291 is shown inserted into the epidural space 293 of an individual using a paramedian approach. Here, the epidural space is the potential space for this specific procedure. The distal end of the access cannula opens toward the dura 310 of the spine a short distance away from the surface of the dura over which the assembly 40 is to be deployed. It should be understood that the structure of the access cannula 291 is not part of the current invention. Any tool for creating an opening, a portal, into the patient that is directed to the location where the assembly 40 is to be deployed may perform the function of access cannula 291.

Once the tip of the access cannula 291 is disposed adjacent and directed towards the target tissue, sheath 154 with the components encased therein, followed by shaft 160, is pushed through the lumen of the cannula 291. Forward force to advance the sheath 154 is applied through shaft 160. This force may come from a handle (not shown) located outside of the body that is attached to the proximal end of the shaft 160. Prior to, or soon after the initiation of these steps, the proximal free ends of the steering cables 256 are tied to a steering unit, not illustrated and not part of this invention. This steering unit selectively places a tension on the steering cables 256. In some versions of the invention, the handle through which force is transferred to shaft 160 and the steering unit are an integrated assembly.

Figure 23:
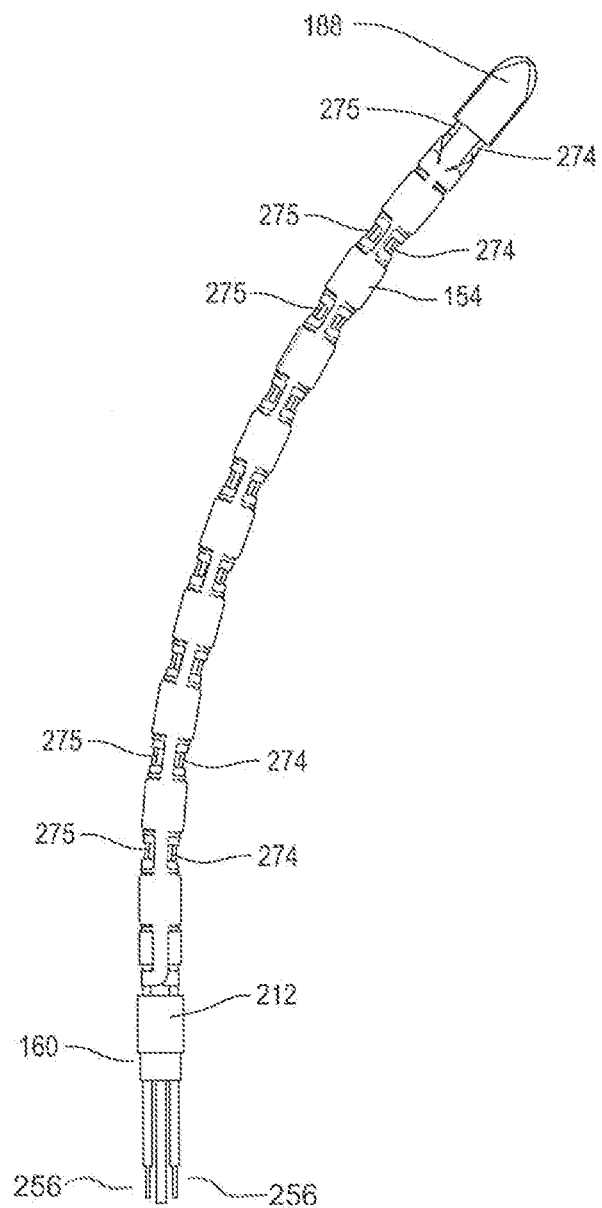
FIG. 23 illustrates how the steering assembly of this invention operates.

As the sheath-encased electrode array 40 exits the access cannula, the steering cables 256 are used to direct the delivery of the array. This is represented in FIG. 23. Specifically, by pulling on one of the cables 256, a proximally directed force is placed on the side of the front anchor 188 to which the pulled cable is attached. Rear anchor 212 functions as a fulcrum around which the pulled on cable 256 bends. In FIG. 23, the right side cable 256 is depicted as the cable subjected to the pulling force. As a result of the side loading placed on the front anchor by this pulling, core 152 is flexed to the side of the pulled cable. More particularly, as a result of the side loading a moment is created. This moment flexes, bends the core links 168 towards that side of the core 152. The bending of the core 152 results in a like bending of the electrode array 40 folded over the core and the sheath 154 disposed over both the array and the core.

Again, it should be appreciated that when the cables 256 are bent, the bending does not occur in the portions within the islands 166. The bending, the flexure, of the cables 256 as well as the core 152 itself, occurs in bending of the links 168 that connect the islands. Each island 168 can be considered a mini-fulcrum. This is why, in FIG. 23, cables 256 are not shown as being bent as continuous curves but rather as a number of short linear segments that are angled relative to each other. The vertices of the right side cable 256 being called out as cable sections 274. The vertices of the left side cable being called out as cable sections 275. Each vertex 274 and 275 is located within a separate one of the core notches 174. Each notch-defining section of core can be considered a flexure section, a section within the core 152 that is contiguous with a cable bore 182 that is more flexible than an adjacent section of the core. When one of the cables 256 is placed in tension, the cable bends within these flexure sections.

As discussed above, the widths of the bridges 54, 56 and 58 adjacent the distal end of the array 40 are narrower than the widths adjacent the proximal end. The narrower widths of these distal end sections of bridges 54, 56 and 58, provides the distal end of the array 40 with increased flexibility that facilitates the ability of the array to move around obstacles.

During the forward advancement of the assembly, the assembly may reach a tissue structure around which it may be difficult to steer. In this event, shaft 160 may be rotated so as to cause a like rotation of sheath 154 and the enclosed array and core 152. Then, by manipulating the steering assembly, the sheath and components encased therein can be flexed vertically, as opposed to laterally. This allows the assembly to be steered over or under the obstruction. By further angling of the assembly, the assembly may be simultaneously steered both vertically and laterally.

This ability to direct the front end of the sheath-encased array 40 allows the assembly 40 to be steered away from tissue and structures that would obstruct forward travel. This also allows the electrode array to be positioned over target tissue off center with respect to the opening in the access cannula from which the assembly is discharged.

The ability to direct the front end of the assembly also reduces the need to force the array and deployment assembly through tissue between the access cannula and the target tissue. Not having to force these components through the tissue reduces the instances of these tissues, as a consequence of the delivery process, becoming damaged.

During the process of positioning the sheath-enclosed electrode array 40 over the target tissue, surrounding tissue may press against the sheath. Alternatively, the sheath may bend or flex. The thickness of the core 152 prevents these forces from compressing the folded over electrode array to the point where the electrode array frame 96 plastically deforms. Frame 96 is prone to such deformation. The limiting of the bending of array does more than reduce the likelihood that the frame 96 will plastically deform. It likewise reduces the likelihood that, as a result of the folding or rolling of the electrode array, the array components on the frame, the electrodes and conductors, will similarly plastically deform.

Once the electrode array 40 is positioned over the target tissue, electrode array 40 is unwrapped from sheath 154.

This process starts by the retraction of the retention bar 158 from sheath 154. This step is performed by pulling on the end of retention bar 158 that extends outside of shaft 160 or the tether attached to bar 158. Simultaneously with the retraction of the retention bar 158, it may be necessary to impose a restraining force on the shaft 160 to prevent the shaft from moving backwards with the retention bar.

As the retention bar 158 is removed, the sheath is able to open. The potential energy in the assembly beams 62 is released. This energy pushes the assembly bridges 54 and 58 outwardly, away from the undersurface of core 152. As seen by reference to FIG. 24, as the bridges 54 and 58 unfold from the core, the outer edges of the outer tabs 60 integral with the bridges 54 and 58 push against the adjacent inner surface of the rib 288-defining section of sheath 154. The outer tabs integral with bridges 54 and 58 thus act as levers that push the unfolding electrode array away from rib 288. This causes tabs 60 integral with bridge 56 to push against sheath flaps 284. This action pushes the flap 284-defining opposed ends of sheath 154 away from each other.

Figure 24:
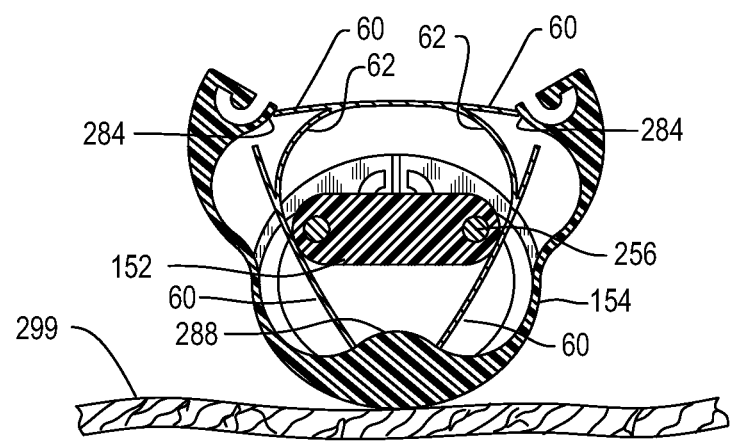
FIG. 24 is a cross-sectional view of an intermediate stage of the electrode array unfolding process of this invention.

Another effect of the levering action of the tabs 60 integral with bridges 54 and 58 is that core 152 is pushed upwardly, away from sheath rib 288. In FIG. 24 and companion FIG. 25, the view is looking toward the proximal end of delivery assembly 150. Accordingly, in these views the unfolded forwardly directed faces of the unfolded proximal portion of sheath 154 are seen.

Figure 25:
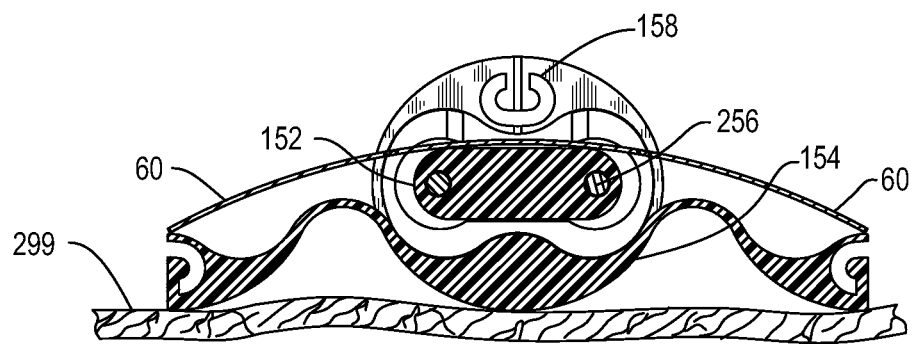
FIG. 25 is a cross-sectional view of the electrode array at the completion of the unfolding process.

As the electrode array 40 continues to unfold, the outer tabs 60 integral with bridges 54 and 58, continue to move laterally outwardly against the inner surface of the sheath. This movement by the tabs 60 results in the continued pushing of the opposed ends of the sheath 154 away from each other. Thus, as depicted in FIG. 25, as a consequence of the complete unfolding of the electrode array 40, the sheath is unwrapped against the surface of the tissue below the assembly 40. Assembly bridge 56 and the tabs 60 integral with bridge 56 remain disposed over core 152. Core 152 remains disposed over the longitudinally extending middle of the unfolded sheath 154.

Owing to how the electrode array was folded, at this time, the electrodes 42 are downwardly directed, towards the unfolded sheath 154 and underlying target tissue, here dura 299.

Deployment of the electrode array 40 continues with the extraction of core 152, sheath 154 and anchors 188 and 212. This part of the deployment process involves pulling rearwardly, proximally, on shaft 160. At this time, to prevent rearward movement of the electrode array 40, a force is applied to the cable 132 to prevent rearward movement of the cable and, by extension, the array.

As a consequence of shaft 160 pulling the rear anchor 212 back and the holding of drive module 44 static, the rear anchor moves rearward relative to the drive module. During this process, anchor wedge 244 is driven underneath the downward face surface of the drive module 44, the surface directed towards the underlying tissue. Anchor wedge 244 thus forces the drive module 44 out of the anchor void space 226.

Figures 26A, 26B:
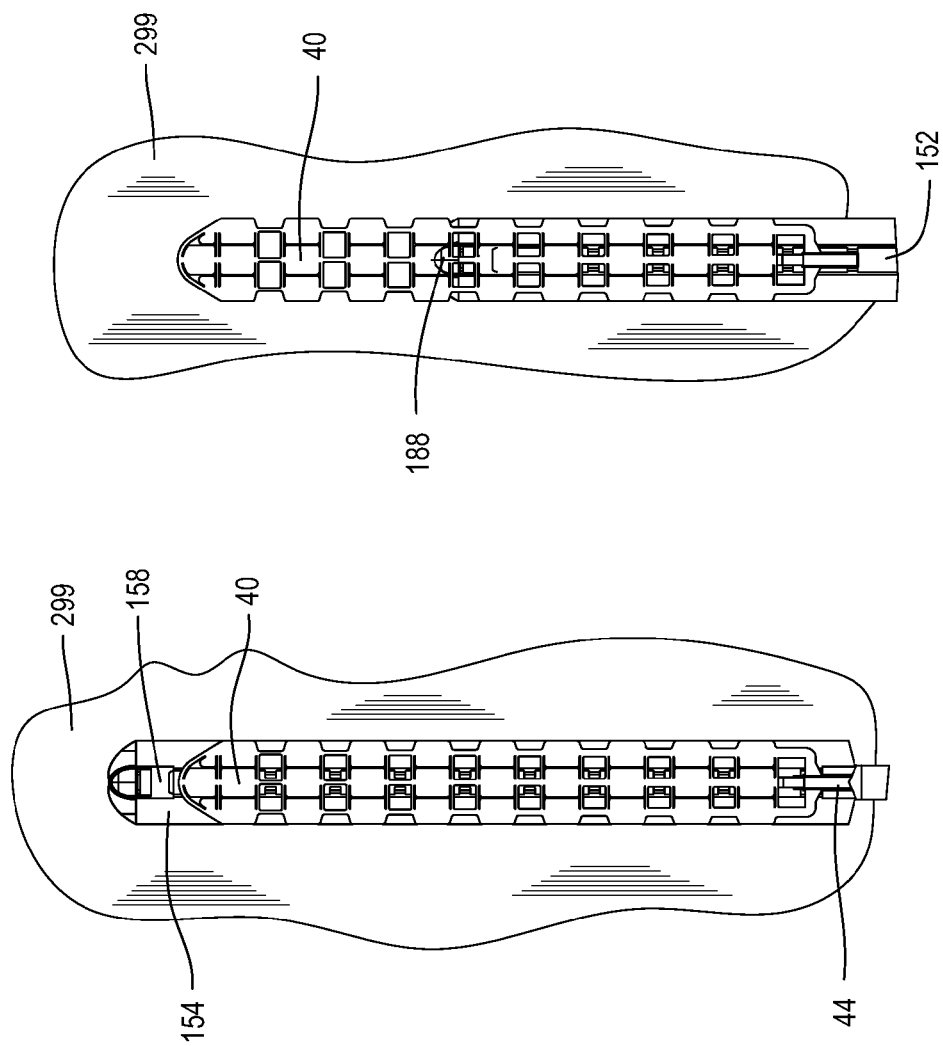
FIGS. 26A through 26D are a set of plan views that illustrate the retraction of the core and the unfolded sheath from between the unfolded electrode array and the tissue through which the current is to be flowed.
Figure 26C:
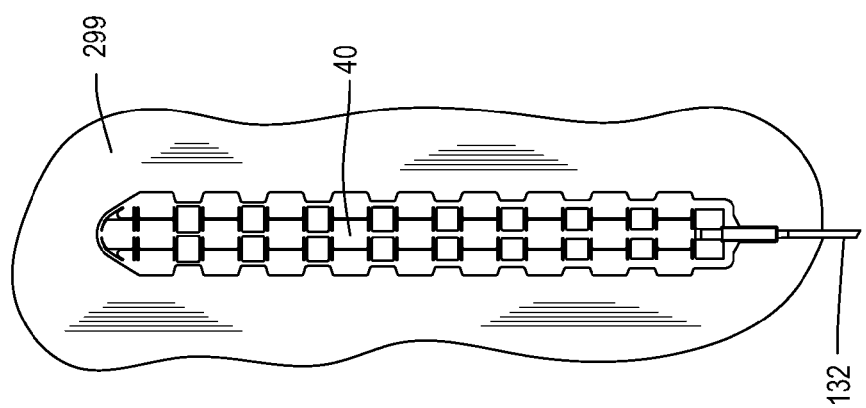

The rearward displacement of rear anchor 212 results in a like displacement of core 152 and front anchor 212. Since the force applied to cable 132 holds the drive module 44, the rest of the electrode array 40 is likewise held static relative to the target tissue. Thus, during an initial part of this displacement of core 152 and front anchor 188 relative to assembly 40, front anchor 188 abuts the assembly head 72 and shoulders 78. Assembly head 72 and shoulders 78 ride up on anchor ramp 195. As front anchor 188 continues to move below assembly 40, the anchor top surface 193 runs under the assembly electrodes 42 integral with bridge 56 as seen in FIGS. 26A through 26C. The assembly frame 96, when unfolded, is wider than front anchor recess 199. Accordingly, the assembly frame 96 and the components attached thereto, do not fall into anchor recess 199. In FIGS. 26B and 26C to illustrate the relative positions of electrode array 40, core 152 and the unfolded sheath 154, the core and sheath are seen "through" the electrode array. In reality, the components underneath the unfolded electrode array 40 may not be visible.

Figure 26D:
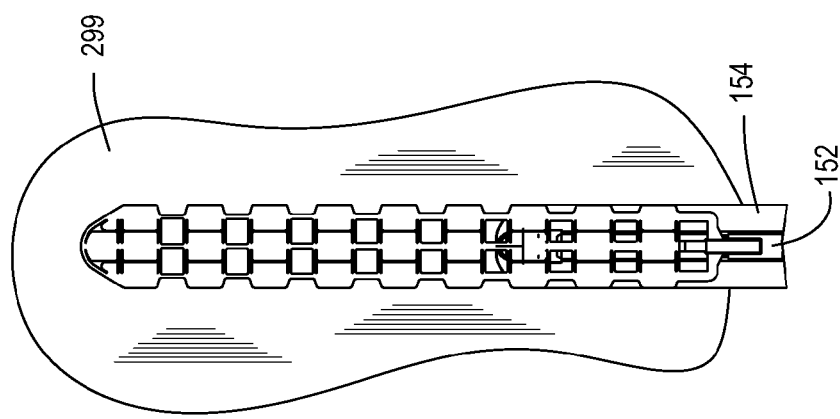

As core 152 and front anchor 188 move under the electrode array 40, the assembly 40 rests on the tissue through which the current will be flowed as is seen in FIG. 26D, here, dura 299. As the distal end of the array lowers onto the tissue, the array settles on the surrounding tissue. This settling of the array reduces the extent to which, as the sheath extraction process continues, a force needs to be applied to cable 132 to hold the array in place.

Eventually, front anchor 188 moves below the assembly drive module 44. Owing to the relative dimensions of the drive module 44 and front anchor recess 198, the drive module 44 may drop into the recess. Owing to the presence of the inclined surface that forms the front end of recess 198, as the anchor travels rearward, the drive module 44 moves out of the anchor recess.

During this retraction process, it should be understood that shaft 160, as well as the steering cables 256 contained therein, are retracted back into the access cannula 291. Eventually core 152, sheath 154 and anchors 188 and 212 likewise approach the distal open end of the access cannula 291. It should be understood that the distal end opening of the access cannula 291 is narrower in diameter than the side-to-side width of the unfolded sheath 154. As a consequence of the geometry of sheath side slits 276, the unfolded proximal ends of the sheath have a tapered profile; their widths increase distally. As the unfolded sheath 160 is drawn into the access cannula 291 this tapered profile facilitates the folding of the sides of the sheath into the narrow width open end of the cannula 291.

At the end of the deployment process, cable 132 remains in place through the portal in which the access cannula was located. The conductors internal to cable 132 are connected to the IDC 134. During the electrode array 40 deployment process the IDC 134 may be implanted during a procedure not part of the current invention. Once the electrode array 40 is connected to the IDC 134, current is driven between the electrodes 42 so that the resultant current flow through the tissue provides the desired therapeutic effect.

Electrode array delivery assembly 150 of this invention is thus designed so that, once electrode array is discharged from the access cannula 291, the array can be steered to a position either side of the center axis of the access cannula. This means the access cannula does not need to be positioned to be in line with the target tissue. Instead, the array, prior to deployment, can be positioned in a space contiguous with, though spaced from, the target tissue and steered over the target tissue. This invention makes it possible to deploy a large surface area electrode array using minimally invasive techniques in locations where previously it may not have been possible.

In the described version of the embodiment, the steering of the core 152 is the result of the bending of the island-connecting links 168. Islands 166 themselves are not subjected to appreciable flexure. As mentioned above, the electrode-carrying tabs 60 are located on the opposed sides of the islands 166. Accordingly, since the islands themselves are not appreciably flexed during the steering process, the array electrodes 42 are likewise minimally flexed. Thus, this invention is further designed to minimize the extent that the bending of the electrode array during steering stresses the electrodes 42.

Delivery assembly 150 is further designed so that, when the electrode array 40 is encapsulated in sheath 154, the array is wrapped around core 152. Collectively, the array and core 152 are shaped so as to, when the array is in this state, limit the bending of the array carrier 96. The limiting of the bending of the carrier prevents the plastic deformation of the carrier. If this deformation were allowed to occur, it could limit the ability of the array 40, to when released from the sheath 154 unfold into the desired deployed state.

During the steering of core 152, the portions of the assembly bridges 54, 56 and 58 over the opposed faces of the core links 168 are subjected to flexure induced bending. The tab free edges of the bridges and the conductors 88 on these sections are relatively close to the longitudinal axis, the neutral axis of the core 152. More specifically, the bridges 54, 56 and 58 are ideally centered over the longitudinal axis of the core 152. Assuming a maximum bridge width of 0.8 mm this means that the outer side surface of a bridge 54 56 or 58 is no more than 0.5 mm away from the longitudinal axis of the core. The reason the distance is not simply one-half the bridge width is to account for any imprecision in the alignment of the bridges over the core. Given the proximity of these components of the array 40 to the axis around which the array is bent, they are minimally stressed during the flexure of the array. This minimal flexing of these components reduces the likelihood of their breakage. Accordingly, this flexure of the electrode array 40 is not likely to damage the assembly.

Still another feature of the assembly of this invention is that the electrode array 40 remains encased in the sheath 154 until the assembly 40 and sheath 154 are disposed over the target tissue. This reduces the likelihood that, as the assembly 40 is moved towards the target tissue, contact with adjacent tissue can damage the assembly 40 or vice versa.

IV. Alternative Embodiment

Figure 27:
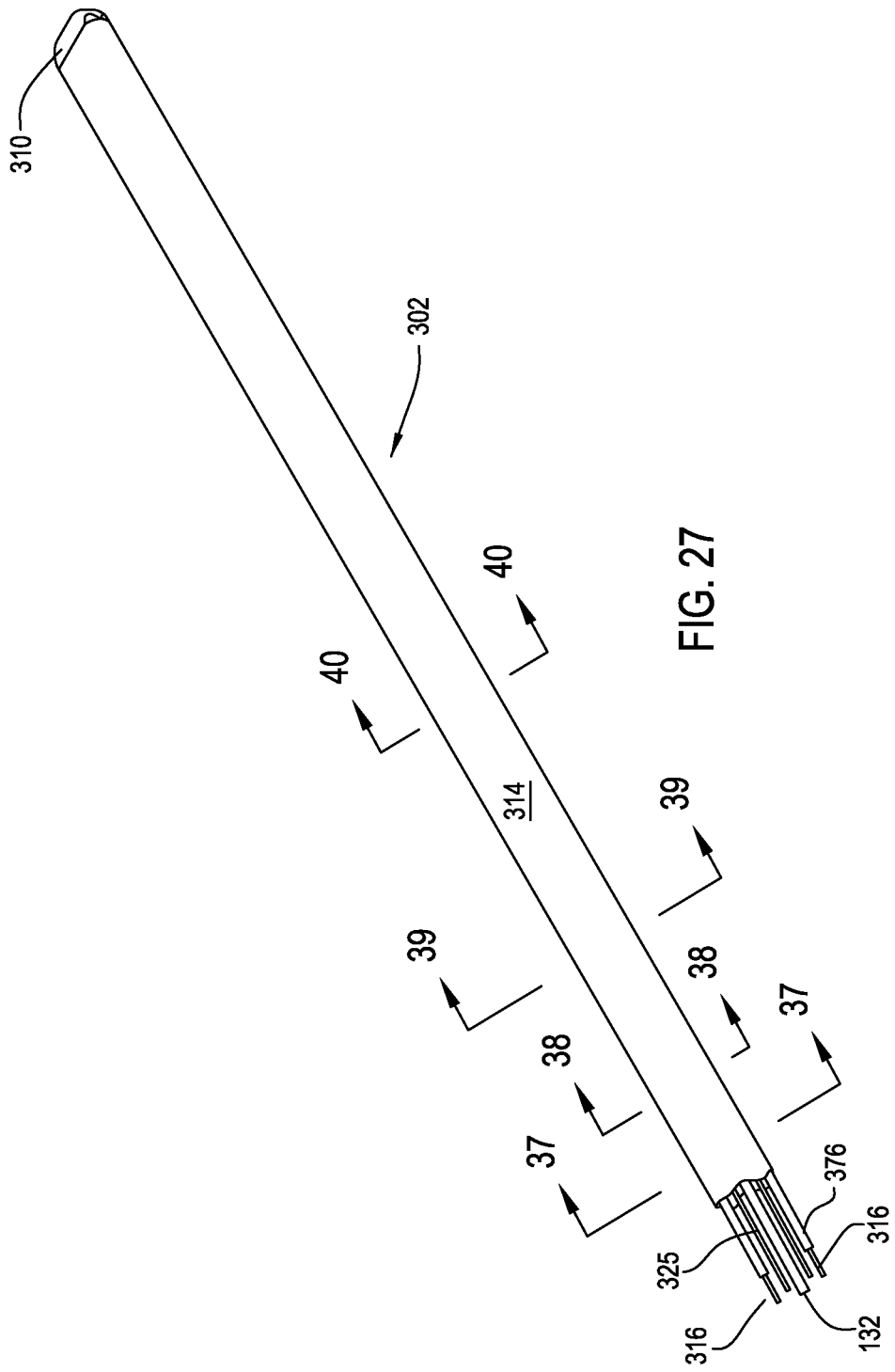
FIG. 27 is a perspective view of an electrode array encased in an alternative delivery assembly of this invention.
Figure 28:
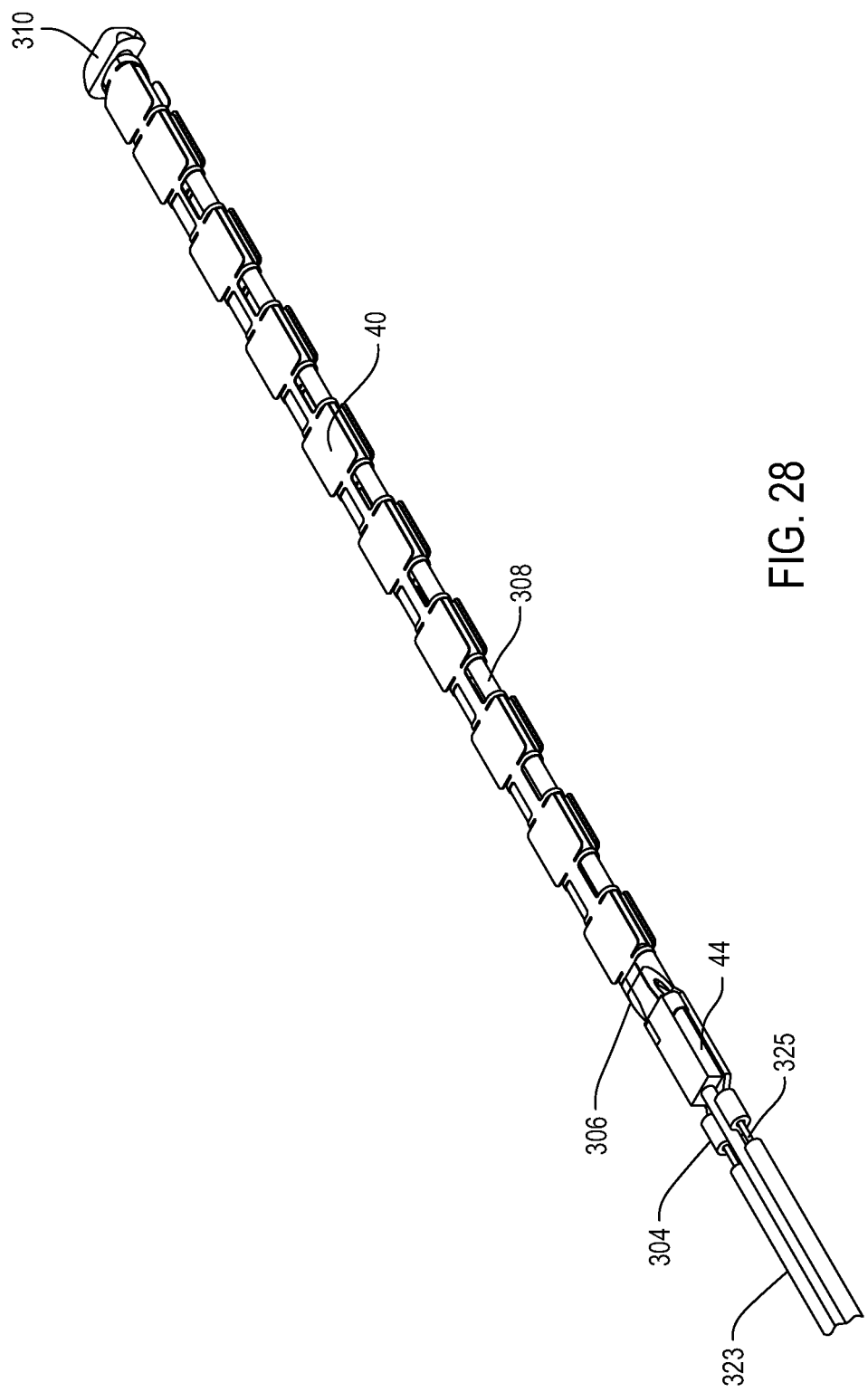
FIG. 28 is a perspective view of an electrode array wrapped around the core of the delivery assembly of FIG. 27.

FIGS. 27 and 28 illustrate how electrode array 40 is encased in an alternative delivery assembly 302 of this invention. Delivery assembly 302 includes a flexible core 308 formed partially from a doubled over length of wire. Array 40 is wrapped around core 308. As seen in FIGS. 28 and 29, two spacers 304 and 306 extend over opposed sections of the core-forming wire. One spacer, a proximal spacer 304, is proximal to the array 40. The second spacer, distal spacer 306, is spaced distally forward of spacer 304 and. When the array 40 is wrapped around core 308, drive module 44 is disposed between the proximal and distal spacers 304 and 306, respectively. A head 310 is the most forward component of delivery assembly 302. Head 310 is the component around which wire 320 that forms core 308 is looped.

Also part of delivery assembly 302 is sheath 314. Sheath 314 extends over the folded over array 40 and the underlying core 308. Disposed inside sheath 314 are steering cables 316. During the deployment process, tensions are placed on the steering cables 316. These tensions flex, steer, the sheath 314 so as to result in simultaneous steering of the encased array 40 and core 308.

Figure 35:
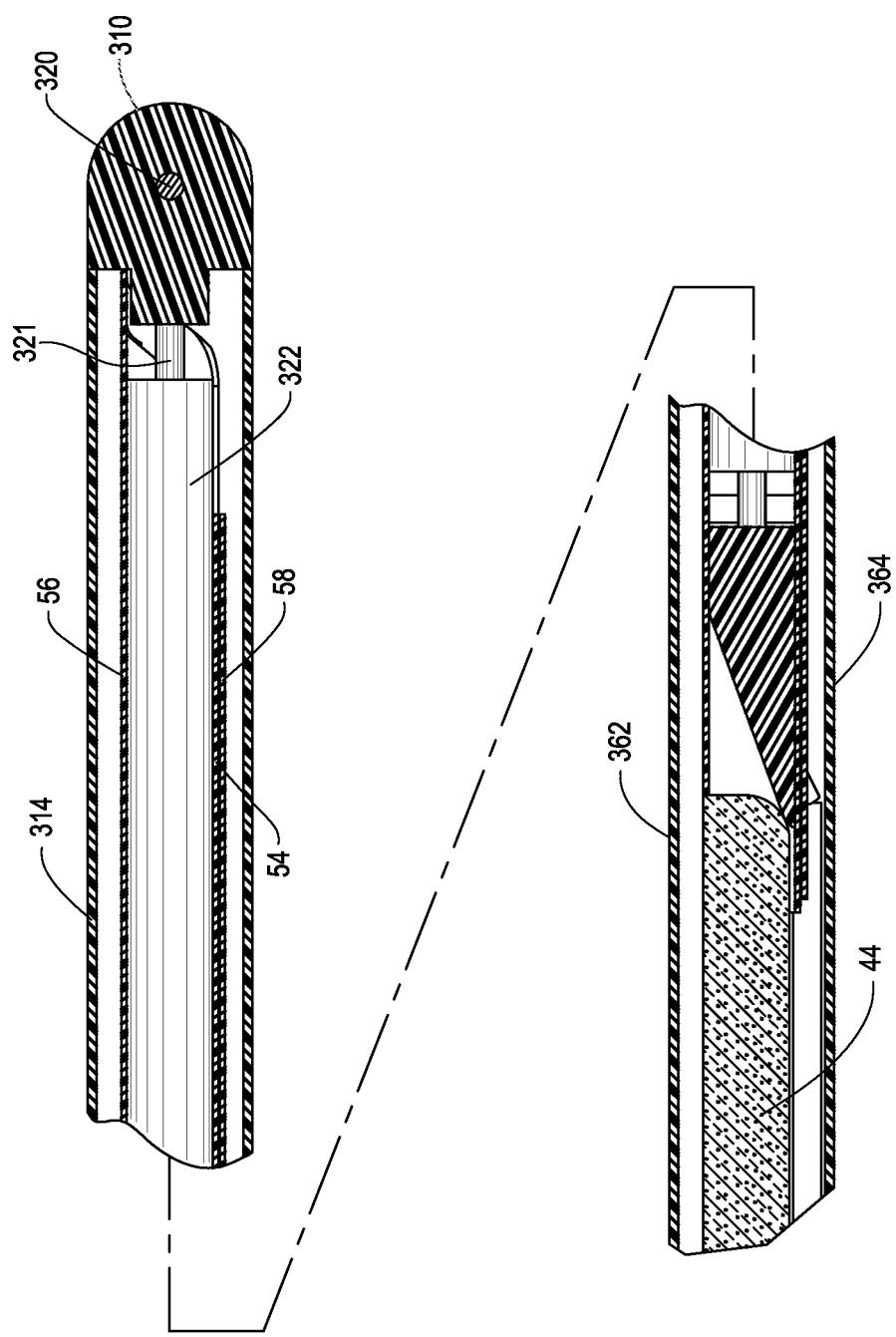
FIG. 35 is partial cross sectional view of the array encased in the sleeve of the delivery assembly along the longitudinal axis of the assembly when viewed in a vertical plane.

Core 308, now described with respect to FIGS. 29 and 40, is formed from wire 320 that has a number of sections. In one version of the invention, wire 320 is stainless steel wire that has a diameter of 0.2 mm. Wire 320 is bent to have two elongated parallel sections 321, (one identified in FIG. 35), that are parallel to each other. A sleeve 322 formed from electrically insulating material is disposed over each wire section 321. Each sleeve 322 is formed from a flexible polymer and has an outer diameter of approximately 1.5 mm. More particularly, wire 320 and sleeves 322 are shaped so that when the array 40 is wrapped around the core 302 each bridge 54, 56 and 58 is disposed over the longitudinal axis that extends between and parallel with sleeves 322. Each pair of electrode-supporting tabs 60 at least partially subtends one of the sleeves 322. When the array 40 is so wrapped the beams 62 conform around the outer surfaces of the sleeves 322. Sleeves 322, which form the opposed curved side surfaces of core 308, are dimensioned such that, when the array beams 62 are so wrapped, the beams are not bent to the extent that the beams undergo plastic deformation.

Delivery assembly 302 is further formed so that the additional parallel sections, sections 325, of the core-forming wire 320 extend proximally rearward of proximal spacer 304. Wire sections 325 extend to a driver, not illustrated and not part of this invention. The driver is the device used to advance the encased in delivery assembly 302 array 40 in the patient towards the tissue against which the array is to be deployment. The driver also includes the assembly used for positioning the encased in delivery assembly array over the tissue against which the array is to be deployed. Typically the driver is designed to be held in one hand so the practitioner using control members mounted to the driver both advances and steers the delivery assembly 302 and array 40 encased therein.

A sleeve 323 extends over each wire 320 proximal section 325. Sleeves 323 are formed from the same material as and have the same dimensions as sleeves 322. Each sleeve 323 extends distally forward from the driver over the associated wire section 325. (In FIG. 27, sleeves 323 are omitted for ease of illustration.) Each sleeve 323 has a distal end that terminates at location approximately 2 mm rearward of the rearwardly directed face of the adjacent proximal spacer 304.

Proximal spacer 304, now described by reference to FIG. 30 is formed from a single piece of biocompatible plastic such as nylon. Spacer 304 is shaped to have two cylindrically shaped fingers 324. Fingers 324 are oriented relative to each other such that the longitudinal axes of the fingers are parallel. A web 326 extends between and connects the fingers 324. The proximal spacer 304 is shaped so the one face of the web 326 extends along a line that is a common tangent line to the outer surfaces of the fingers. The opposed face of the web 326, the face visible in FIG. 30, has a concave profile. This concave face of the web 326 thus defines a U-shaped groove 328 that is centered over and extends longitudinally above the web. Groove 328 is dimensioned to receive the cable 132 extending from array 40.

The proximal spacer 304 is further formed so that a bore 330 extends through each of the fingers 324. Each bore 330 extends axially longitudinally through the finger 324 with which the bore is integral. Each bore 330 is dimensioned to receive a section of the core-forming wire 320, (wire section not identified).

Figure 31:
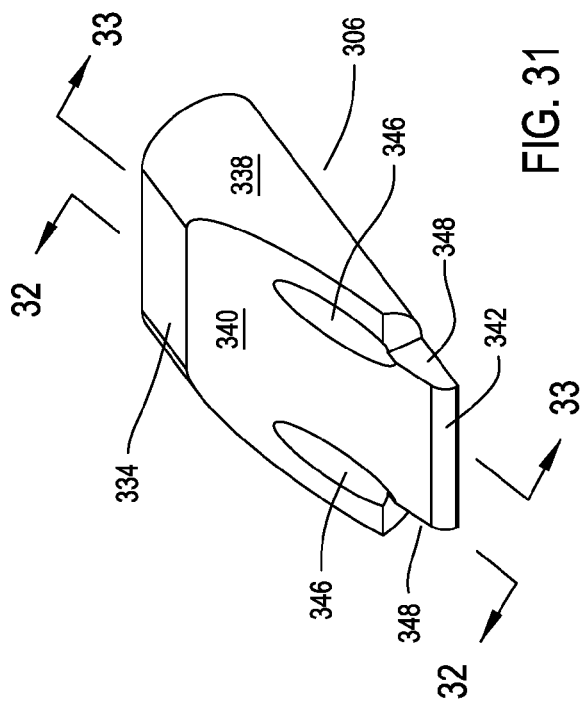
FIG. 31 is a perspective view of the distal spacer of FIG. 29.
Figure 32:
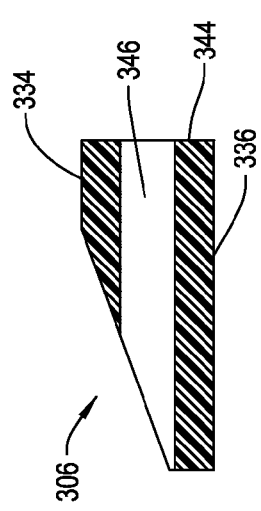
FIG. 32 is a cross sectional view of the distal spacer taken along line 32-32 of FIG. 31.
Figure 33:
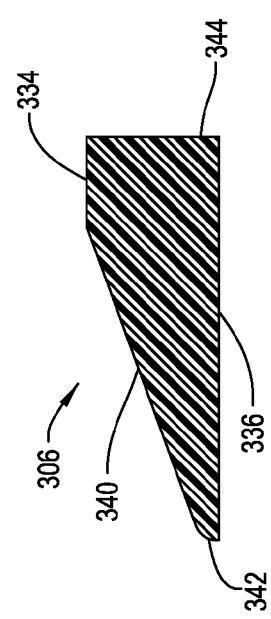
FIG. 33 is a cross sectional view of the distal spacer taken along line 33-33 of FIG. 31.

Distal spacer 306, now described by reference to FIGS. 31-33, is formed from the same material from which proximal spacer 304 is formed. The distal spacer 306 is generally in the form of a block of material with parallel opposed planar top and bottom surfaces 334 and 336, respectively. While surfaces 334 and 336 are parallel, top surface 334 is shorter in length than bottom surface 336. Extending longitudinally between the top and bottom surfaces 334 and 336, respectively, spacer 304 has side surfaces 338. Side surfaces 338 which are symmetric with each other, have a convex profile such that they extend outwardly from top surface 334 and bottom surface 336.

The distal spacer 304 is further shaped to have a proximally directed face 340. Proximally directed face 340 extends diagonally downwardly and proximally from top surface 334. Proximally directed face 340 does not extend to the proximal end of bottom surface 336. Instead, a rim 342 extends a short distance upwardly from the proximal end of bottom surface 336 to the adjacent end of proximally directed face 340. Rim 342 has an outer surface that curves upwardly and distally from the proximal end of bottom surface 336. A distally directed face 344 forms the distal end of spacer 304. Distally directed face 344 extends perpendicularly between top surface 334 and bottom surface 336.

Two parallel bores 346 extend longitudinally through distal spacer 304. Bores 346 have the same diameter as proximal spacer bores 330. Bores 346 are spaced apart the same distance which bores 330 are spaced apart. The opposed ends of bores 346 open into proximally and distally directed faces 340 and 344, respectively, openings not identified. The distal spacer 304 is further formed so that below where each bore 346 opens into the proximally directed face 340 there is a notch 348 in the spacer. Notches 348 thus extend upwardly from the spacer bottom surface 336 to the proximally directed face 340.

Figure 34:
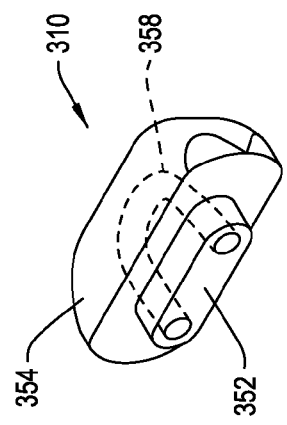
FIG. 34 is a perspective view of the head of FIG. 29.

Head 310 may be formed from the same material from which spacers 304 and 306 are formed. As seen in FIG. 34, head 310 is formed to have a base 352. Base 352 has an oval cross sectional shape. The major axis of base 352 is approximately equal to the distance across the outermost surfaces of the two parallel sleeves 322. Forward of base 352, head 310 has a nose 354. Nose 354 has an oval cross sectional shape. Adjacent base 352 the major and minor axes of nose 354 are greater than that of the base. Extending distally forward, the diameters of the nose decrease and merge into a tip 356 with a rounded surface.

The head 310 is formed to have a U-shaped bore 358, shown in phantom. Bore 358 has an opening on one side of the proximally directed face of base 352 and extends into nose 354. Head 310 is further shaped so that bore 358 curves around to have a second opening in the opposed side proximally directed face of base 352. Bore 358 is dimensioned to receive the core-forming wire 320. AS discussed below, head 310 may be molded in place over wire 320. The molding of the head 310 in place serves to define bore 358.

Sheath 310 of delivery assembly 302 is formed from a biocompatible polymer such as nylon. As seen best in FIGS. 36 and 41, sheath 310 has a generally oval cross sectional shape so as to have, in cross sections perpendicular to the longitudinal axis through the sheath, a minor axis across said sheath that is relatively short in length and a major axis across said sheath that is longer in length than the minor axis. More particularly, the sheath is shaped to have parallel top and bottom panels 362 and 364, respectively. Panels 362 and 364 each have a thickness of approximately 0.15 mm. Side panels 366 extend between the top and bottom panels 362 and 364, respectively. Each side panel 366 curves outwardly relative to the edges of the adjacent top and bottom panels 362 and 364. Generally the side panels 366 are thicker than the top and bottom panels 362 and 364, respectively. Sheath 310 is further formed so that each side panel 366 has an inwardly extending rib 368. Each rib 368 projects away from the side panel 366 with which the rib is associated so that ribs are directed toward each other. A bore 370 extends through each rib 368. Bores 370 thus extend longitudinally through the opposed sides of sheath 310 adjacent the opposed ends of the sheath major axis.

Sheath 314 is shaped so that the minor axis in the lumen 315 defined by the sheath, the distance between the adjacent inner faces of top panel 362 and bottom panel 364 is slightly greater than the width across the array 40 when folded over the core 308. In some versions of the invention, this lumen width is approximately 0.5 mm greater than the distance between the outer surface of bridge 56 and the outer surface of the outer of the two folded under bridges 54 or 58. This lumen width is such that, when the array is disposed in the sheath 314, the lumen prevents the superelasticity of the carrier from unfolding the array 40. In FIGS. 37-40, for ease of illustration, gaps are shown between the outer surface of bridge 56 and the adjacent inner surface of the sheath and between the bridge 58 and the sheath.

Delivery assembly 302 is constructed so that sheath 314 extends proximally rearward from the proximal spacer 304. More particularly, the delivery assembly 302 is constructed to extend over the proximal sections 325 of wire 320. In some versions of the invention, sheath 314 extends back to the driver.

Each steering cable 316 is disposed in a separate one of the sheath bores 370 so that the cables are located adjacent the opposed ends of the major axis. Each cable 316 is formed from stainless steel and has a diameter of 0.15 mm. Cables 316 extend out from the proximal end of sheath 314 and are connected to the steering assembly. Each steering cable 316 extends through the associated bore 370 to the distal end of the bore.

Figure 36B:
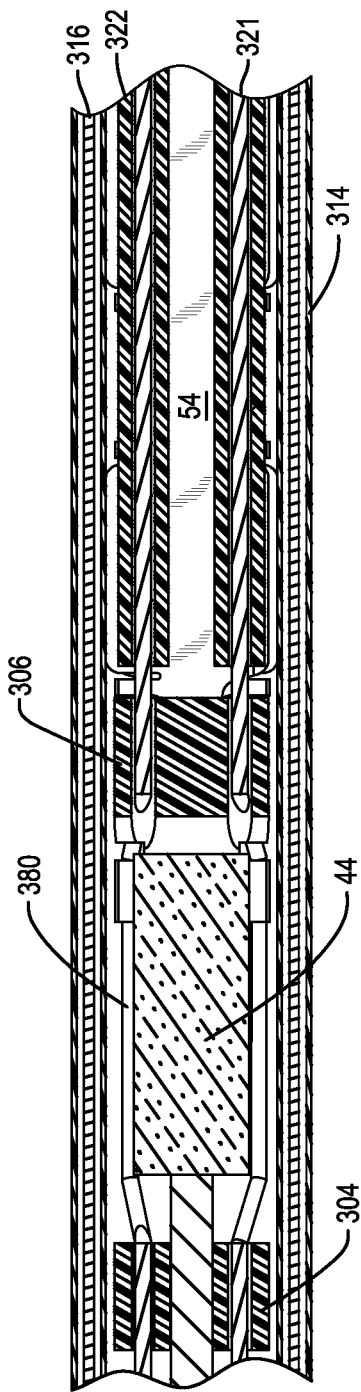
Figure 36C:
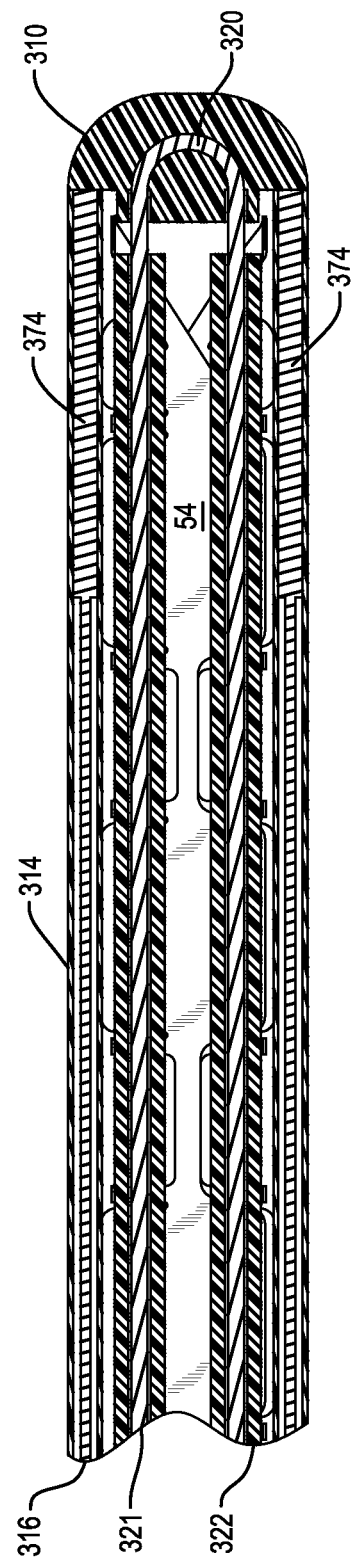
Figure 37:
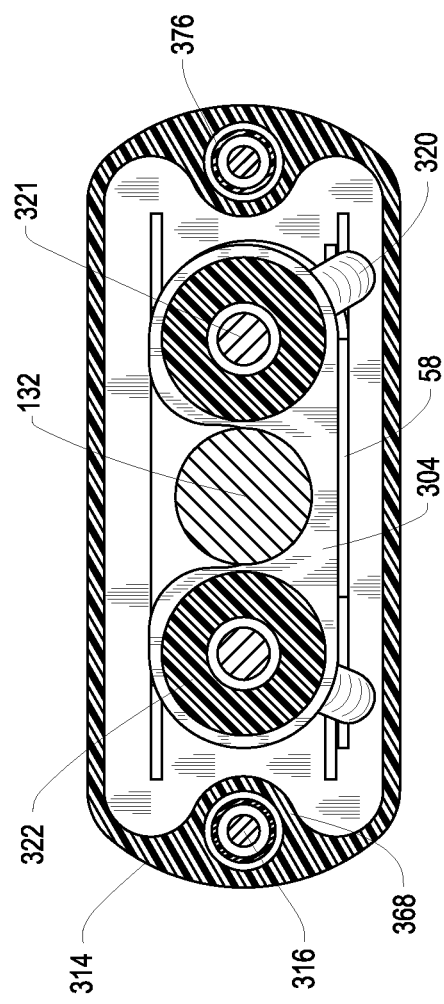
FIG. 37 is a cross sectional view of the encased array when viewed along line 37-37 of FIG. 27.

An anchor 374 holds the distal end of each steering cable 316 in the distal end of the associated sheath bore 370. In one version of the invention, the anchor 374 comprises a strand of wire wrapped around the distal end of the cable 318. This wire may be a preformed coil spring. Solder secures the spring to the steering cable 316. Consequently the anchor 374, as depicted in FIG. 36B has an outer diameter larger than that of the steering cable 316. In FIG. 36b for ease of illustration the anchors 374 are seen simply as large diameter plugs at the end of the cables 316 with which the anchors are integral. The outer diameter of each anchor 374 is, relative to the sheath bore 370, sufficiently large so that the portion of the sleeve that defines the bore holds the anchor in place. In some versions of the invention, an adhesive, such as epoxy, is further used to hold each anchor 374 in the distal end of the associated sheath bore 370.

A sleeve 376 extends longitudinally over each cable 316. Sleeves 376 are formed from stainless steel or other material that is less flexible than the encased steering cables 316. Collectively, sheath 314, cables 316 and sleeves 376 are constructed so that the sleeve encased cables can seat in sheath bores 370. While not apparent in the drawings, in many versions of the invention, the components forming delivery assembly 302 are constructed so that there is clearance between the outer surface of each steering cable 316 and the adjacent inner wall of the surrounding sleeve 376. This clearance may be 0.05 mm. This clearance facilitates the movement of the cable 316 in the sleeve. There is also a clearance between the outer surface of the sleeve 376 and the adjacent internal wall of the sheath 314 that defines the bore 370 in which the sleeve is seated. This clearance facilitates the seating of the sleeve 376 in the bore. In some versions of the invention, the outer diameter of each sleeve 376 is 0.05 mm relative to the sheath bore 370 in which the sleeve 376 and associated cable 316 is seated.

Each sleeve 376 extends distally forward from the driver or other steering assembly from which delivery assembly 302 extends. Sleeves 376 do not over the whole of steering cables 316. Instead, the sleeves 376 terminate at a location proximal to the proximal spacer 304. In the illustrated version of the invention each sleeve 376 terminates in sheath 314 at a location that is approximately 5 mm proximal to the proximal end of proximal spacer 304.

Flexible core 308 of this invention can be constructed by first bending wire 320 to define the two sections 321 and the two sections 325. Head 310 can be molded in place over the bend in the wire 320 from which wire sections 321 proximally extend. Sleeves 322 are then fitted over wire section 321. First, distal spacer 306 and, then, proximal spacer 304 are fitted over the sections of wire 320 distal to wire sections 321. The sections of wire 320 between spacers 304 and 306 are bent so as to form a cradle 380. More particularly, each section of wire is bent so as to have: a portion adjacent the proximal spacer bore 330 that extends downwardly; a portion that is parallel to and laterally spaced apart from the distally located wire section 321; and a portion that extends upwardly into the adjacent bore 346 of the distal spacer 306, (individual portions not identified). Cradle 380 is shaped to define a space 382 between spacers 304 and 306 in which, when the array drive module 44 can seat.

Electrode array 40 is wrapped around core 308 as seen in FIG. 28. In FIG. 28, the array beams 62 as well as the sections of sleeves 322 between the beams are visible. Also visible are the end sections of distal spacer proximally directed face 340. These components are shown in this Figure in part to show the relative relationships between the components of the array 40 and the components of the delivery assembly 302.

Figure 38:
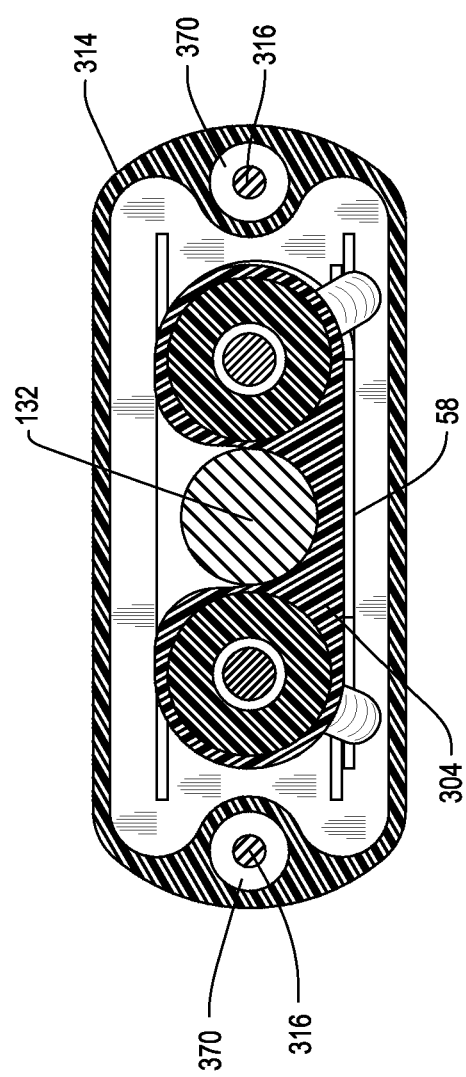
FIG. 38 is a cross sectional view of the encased array when viewed along line 38-38 of FIG. 27.
Figure 39:
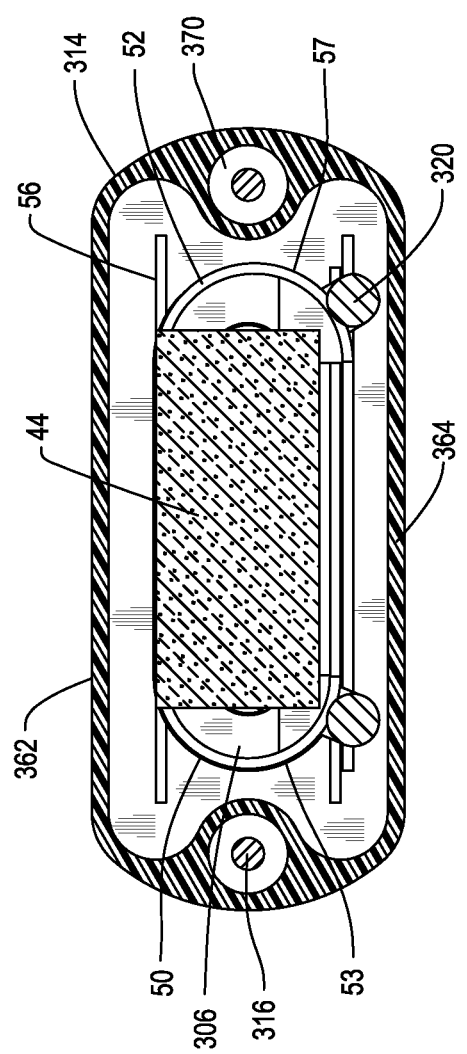
FIG. 39 is a cross sectional view of the encased array when viewed along line 39-39 of FIG. 27.

More particularly, the electrode array 40 is positioned so that bridge 56 is seated over core 308 so that the drive module 44 seats in space 382 above cradle 380 as seen in FIGS. 28 and 39. As a consequence of this seating of drive module 44, as seen in FIGS. 28 and 39, the cable 132 that extends from the drive module 44 seats in proximal spacer groove 328 as seen in FIGS. 28 and 38. Array 40 is wrapped so that first one of bridge 54 or 58 is positioned against the surfaces of core sleeves 322 opposite the surfaces on which bridge 56 rests. Then, the other of bridge 58 or 54 is wrapped against the first wrapped bridge. Bridges 54, 56, 58 are thus understood to lie in planes that will be parallel to the major axis across the sheath 314.

During the process of wrapping the array 40 around the core, the array beams 62 are curved around the outer surfaces of sleeves 322, best seen in FIG. 40. The diameter of sleeves 322 is such that the beams are not curved to such an extent that the array frame 96 undergoes plastic deformation.

Also during the process of wrapping the array 40 around core 308, array feet 53 and 57 and legs 50 and 52 are wrapped around distal spacer side surfaces 338. The distal spacer 306 is formed so that the wrapping of these sections of the array around the spacer again, do not plastically deform the array.

Once the array 40 is wrapped around core 308, sheath 314 is slipped over the array and core 308. Sheath 314 is fitted over the core 308 so that, as seen in FIG. 40, sheaths ribs 368, and the steering cables 316 encased in the ribs, are located outwardly of where the array 40 is wrapped over core 308. The sheath 314 is moved distally forward so that distal end of the sheath is located adjacent the proximally directed step between head base 352 and head nose 354. The fitting of array 40 and core 308 in sheath 314 completes the encasement of the array 40 in the delivery assembly 302.

The delivery assembly-encased-array is then attached to the insertion device. As part of this process, the ends of the steering cables 316 are often attached to an assembly able to place/release tensions on the cables individually. The insertion device is employed to insert the delivery assembly-encased-array in the patient. Specifically, the array 40 is positioned ideally over or at least proximal to the target tissue over which the array is deployed.

If the array needs to be positioned over the target tissue a force is placed on wire section 325. Typically this force is a pushing force. This force pushes the core 308, the array 40 and the sheath 314 forward, towards the target tissue.

During the positioning of the array, it may be necessary to steer the array laterally. In this situation, a tension is placed on one of the steering cables 316. The anchored distal end of the cable 316 pulls on the adjacent end of sheath 314. The sleeve 376 in which the cable 316 is partially encased limits the extent to which the encased section of cable can flex. Distal to sleeve 376, the cable 316 is able to more freely flex. Thus, the sleeve free distal end of each core bore 370 can be considered the flexure section, the portion of the sheath 314 within which the cable in tension bends. The bending of cable 316 results in a like bending of the distal end of sheath 314 and its contents, array 40 and core 308. This bending of sheath 314 and its contents is the steering of delivery assembly 302. By selective advancement and steering of the sheath, delivery assembly 302 is positioned so that array 40 and core 308 are disposed over the tissue over which the array 40 is to be deployed.

Once the array 40 is properly positioned, the deployment process continues with the extraction of sheath 314. This step is accomplished by pulling proximally on the sheath 314 so it retracts away from core 308. To prevent the retraction of the array 40 and core 308 it may be necessary to simultaneously impose a restraining force of the proximal ends of wire sections 325. The retraction of the sheath 314 away from core 308 frees the array 40. Since the array 40 is no longer constrained, the potential energy in the folded carrier 96 is released. This energy unfolds the array from core 308. This process is essentially identical to the process described with respect to FIGS. 24 and 25 with regard to the array 40 and core 152.

Once the array 40 is unfolded, core 308 is extracted away from the target tissue. This step is performed by pulling proximally on wire sections 308. During the initial part of this step, core head 310 moves under array head 70 (FIG. 1) and distal spacer 306 moves under array drive module 44. Owing to the array 40 being in bowed state, there is a clearance between the array head 70 and core head 310. This clearance allows the core head 70 to move below the array 40. There may not be a clearance between drive module 44 and distal spacer 306. If there is no clearance between these two components, the drive module 44 rides up on the angled proximally directed face 340 of the distal spacer. This allows spacer 306 to travel freely under the drive module 44.

As core 308 is retracted, the head 310 moves below the drive module. There is a clearance between the drive module and the head that allows the head to move freely. Once the core 302 is removed from the patient, array 40 can be considered implanted and deployed. Currents can be driven between the array electrodes, through sections of the target tissue, in order to provide the patient the beneficial effect of the current flow.

Relative to steering cable 256 of delivery assembly 150, cables 316 of assembly 302 are located further from the longitudinal axis of the sheath encapsulated array 40. Consequently, in comparison to when one of the cables 256 is tensioned, when one of the cables 316 is tensioned, there is a greater flexure, bending of the array 40. This increased bending of the array improves the ability of the practitioner to steer around objects that impede the advancement of the array 40.

Core 308 of delivery assembly of this invention is formed out of two sections 321 of one wire 320. When the core 308 is bent, steered, since wire sections 321 are separate from each other, they are able to bend independently. This means the core of this version of the invention is itself more flexible than a core that is formed out of unitary body having the same width as the combined width of the wire sections that form core 308. This flexibility further contributes to the steerability of the delivery assembly and array of this invention.

Core 308 does not have the islands 166 of core 152. Islands 152 limit the flexibility of core 152. This reduced flexibility may, in some instances, be useful to prevent excessive damage-causing bending of the array. It has been found that the sections of the array bridges 54-58 from which tabs 60 extend are, owing to the presence of the tabs themselves relatively inflexible, (in comparison to the tab free sections of the bridges.) This inherent flexibility of the array has been found to be sufficient to prevent the bending of the array to such a degree that the electrodes formed 40 on the array may become damaged.

Further it is believed that it is relatively economical to fabricate the components that form delivery assembly 302 of this invention.

V. Further Alternative Embodiments

It should be understood that the foregoing is directed to specific versions of the invention and that other versions of the invention may have features different from what has been described.

For example, it should be understood that there is no requirement the delivery assembly always be used with the above-described electrode array. An electrode array used with the delivery of this invention may be shaped differently from what has been described. Similarly, there is no requirement that delivery assembly be used with an electrode array that is foldable. Thus in some versions of the invention, the core serves as a support bed for an electrode array that does not unfold. The core or sheath is steered to the target tissue against which the array is to be disposed. Thus the delivery assembly could be used with an electrode array that is cylindrical and that includes a number of arcuately shaped electrodes that extend partially or completely circumferentially around the circumference of the device. Likewise, the delivery assembly could be used to deploy an electrode array that includes a single flat electrode or a single set of longitudinally aligned electrodes. Likewise, in some versions of the invention, the width of the bridges of the electrode array may not vary along the length of the assembly.

Similarly, this delivery assembly could be used with electrode arrays that do not have the drive module or other component necessary for the operation of the array mounted on the surface of the carrier.

It should therefore be appreciated that not all electrode arrays of this invention be provided with carriers that are superelastic. Most, if not all of the electrode arrays will at least have carriers that are flexible.

Similarly, this invention can be used to deliver an electrode array wherein, instead of the current flowing between the electrodes, the current is flowed to the case of a metal housing for the IDC 134. Likewise, in some versions of the invention, electrodes may be disposed on the opposed sides of the complementary support frame.

It may be desirable to adjust the widths of the array beams 62 to adjust of energy they store and subsequently release during the unfolding process.

Furthermore, in some versions of the invention, the energy for unfolding the sheath 154 may not be entirely stored in the electrode array. Thus, in some versions of the invention, embedded in the sheath are superelastic ribs that extend laterally across the sheath. These ribs, in the deployed state are flat. The ribs could even have a reverse curvature, that is, a curvature opposed the direction in which the sheath is wrapped around the electrode array. The wrapping of the sheath around the electrode array stores potential energy in these constrained, wrapped ribs. As a consequence of the release of the opposed sides of the sheath from each other, this potential energy is released to unwrap the sheath. These ribs may be the sole force of sheath-unwrapping energy or supplement the unwrapping force released by the unfolding of the electrode array.

It should similarly be appreciated that the sheath 154 of assembly 150 may be combined with core 308 of assembly 302. Core 152 may be combined with sheath 314. A sheath with embedded steering cables 316 may be provided with a slit and complementary retaining member similar to slit 156 and retaining bar 158 of sheath 154. Similarly, the steering cables 256 may, like the steering cables 316 of delivery assembly 302 be two sections of the same wire. The wire may be bent around front anchor 188. The bent distal end of the steering cable-forming wire is then secured to the anchor. The advantage of having the steering cables 256 and 316 formed out of bent wire is that it increases the reliability of the assembly 152 or 302.

Likewise, there is no requirement that in all versions of the invention, sheaths 154 and 314 be shaped so that their outer profiles, when folded are elliptical. However, it is believed that in many preferred versions of the invention, the sheath will have an elliptical shape. This is because this shape, for many applications, minimizes the size of the portal that needs to be formed in order to deliver the electrode array. Also for many applications of this invention, the elliptical shaped array is one that has a relatively small height, in comparison, to a circular cross section. This small height allows the assembly to be delivered through spaces that themselves are of narrow heights. More particularly, it is believed in many versions of this invention the major axis of the sheath 154 or 308 when disposed over the array and core is a maximum of 6 mm and often 5 mm or less.

It should be appreciated that alternative deployment assemblies of this invention could have more or fewer components than the described version. For example, in some versions of the invention, the structural features of the front and/or rear anchor may be built directly into the core. Likewise, there is no requirement that in all versions of the invention, the core include the described notches so as to facilitate the flexibility of the core.

The shapes of the various components may also be different from what has been described. Thus, the core 152 may have cross sectional shapes different from what has been described, such as an elliptical cross-section. Alternatively, the assembly may be constructed so that the core notches are partially filled. The components filling the core may be more flexible than the island-defining portions of the core. The arrangement of these components, which may be integrally formed with the core, could improve torsional stiffness of the core. Improving the torsional stiffness increases the extent to which the core, when steered, turns to the side as opposed to twists. Also the durometer, the flexibility, of the material forming the core may change along the length of the core. When the core holds the steering cables, these sections of the core formed from material of increased flexibility may be considered the flexure sections of the core.

The dimensions of the components may vary from what has been described above. For example, in versions of the invention wherein the array frame-forming superelastic material is relatively thick, the top to bottom thickness of the core would need to increase. In versions of the invention wherein the array frame-forming superelastic material is relatively thin, the top to bottom thickness of the core could decrease. Again, the key variable is to provide a core that provides sufficient support to prevent the folded-over electrode array 40 from undergoing plastic deformation.

In some versions of the invention a flexible tube (not illustrated) is fitted over the portion of cable 132 disposed in shaft 160. This tube, while being bendable from its longitudinal axis, can withstand some loading along the longitudinal axis without bending. This tube may be made of material such as polyimide. The tube may be positioned to abut the proximally directed face of drive module 44. This tube may be used to push the assembly towards the target tissue.

Similarly core 308 may have constructions different from what has been described. Thus instead of the independently flexible members forming the core being sleeve encased wires, the members may be solid cylinders or hollow tubes of plastic. Likewise, this invention is not limited to assemblies wherein the core 308 consists of just two parallel independently flexible members. Versions of the invention with three or more flexible members forming the core also fall within the scope of this invention. This includes versions of the invention wherein the flexible members are in a common plane. This version of the core may be useful if the electrode-supporting bridges of the array are relatively wide. The three or more flexible core-forming members would provide support for the wide bridges will collectively forming a core that is relatively flexible. Alternatively, the core-forming flexible members may not all be parallel. For example three sleeve encased wire sections 321 may be arranged in a triangle. An advantage of this version of the invention is that it reduces the angle of the arc around which the bridge-connecting beams need to be wrapped. Reducing this arc again serves to reduce the likelihood that such bending of the beams results in their plastic deformation.

Moreover, the invention is not limited to assemblies with two steering cables. It may be possible to provide a version of this invention with a single steering cable. This would allow steering in a single direction. Then, if it is necessary to steer the delivery assembly in a second direction, the assembly would have to be rotated so it could be steered. In some versions of the invention three or more steering cables may be provided. By providing three or more cables, the delivery assembly could be simultaneously steered vertically and horizontally.

Similarly, the structural features that define the flexure sections of the core or sheath may be different from what has been described. For example, it may be desirable to encase a steering cable in a sleeve with sections of varying flexibility. For example, the sleeve may be designed so that extending towards the distal end of the sleeve, the sleeve is progressively more flexible. This type of sleeve can be provided by forming sections of the sleeve out of different materials and/or varying the diameter of the sleeve. Alternatively, in versions of the invention wherein the steering cables are encased in the sheath, discrete sections of the sleeve may cover separate sections of the cables. These discrete sleeve sections are spaced apart from each other. This thus defines in the sheath a number of spaced apart flexure sections.

Furthermore, while the assembly of this invention can be percutaneously inserted in the patient, its use is not so limited. Other minimally invasive procedures may be used to initially position the sheath-containing electrode array of this invention in the body.

Thus, it is an object of the appended claims to cover all such variations and modifications that come within the true spirit and scope of this invention.

What is claimed is:

1. An electrode array and delivery assembly, said assembly comprising:
    a core formed from flexible material, said core having a longitudinal axis that extends proximally to distally, and at least two opposed side surfaces that are laterally spaced apart from each other wherein, one of the side surfaces is a first side surface;
    an electrode array separate from said core, said electrode array including: first and second bridges that, longitudinally, extend proximally to distally and that are laterally spaced apart from each other; at least one first beam formed from elastic material that extends laterally between said first bridge and said second bridge so as to connect said bridges together; at least one first tab that extends laterally outwardly from said first bridge towards said second bridge and that is separate from both said second bridge and said at least one first beam; and an electrode mounted to said at least one first tab wherein, said electrode array is wrapped around said core so that: said first bridge and second bridge are at least partially located in separate spaces between the spaced apart side surfaces of said core so that said bridges at least partially overlap each other; said at least one first beam is wrapped around the first side surface of said core; and said at least one first tab projects away from the first side surface of said core and said at least one first beam;
    a sheath disposed over said core and said electrode array so as to prevent unwrapping of said electrode array from said core; and
    at least one steering cable disposed in said sheath and anchored to said sheath so as to selectively flex said sheath, and
    wherein said sheath is removably disposed over said core and said electrode array so that the extraction of said sheath away from said core and said electrode array allows the release of energy in said at least one first beam so that said at least one first beam unwraps said electrode array from said core so that said core can be withdrawn away from the unwrapped electrode array.

2. The electrode array and delivery assembly of claim 1, wherein:
    said electrode array is formed so that at least one second tab extends laterally outwardly from said second bridge towards the first said bridge, said at least one second tab being separate from said first said bridge, said at least one first tab and said at least one first beam;

an electrode is mounted to said at least one second tab; and said electrode array is wrapped around said core so that said at least one first said tab extends outwardly from a first end of said at least one first beam and a first end of the first side surface of said core and said at least one second said tab extends outwardly from a second end of said at least one first beam and a second end of the first side surface of said core.

3. The electrode array and delivery assembly of claim 1, wherein:

said first bridge has first and second opposed longitudinally extending sides, the first side of said first bridge being directed towards said second bridge;

said at least one first tab extends outwardly from the first side of said first bridge towards the second said bridge;

said first bridge is formed so as to have at least one second tab, said at least one second tab extending outwardly from the second side of said first bridge;

an electrode is mounted to said at least one second tab; and said core and said electrode array are collectively dimensioned so that when said electrode array is wrapped around said core, said at least one first tab extends away from the first side surface of said core and said at least one second tab extends away from a second side surface of said core.

4. The electrode array and delivery assembly of claim 1, wherein:

said electrode array is formed to have: a third longitudinally extending bridge that is separate from said first bridge and said second bridge; at least one second beam formed from elastic material that extends laterally between said second bridge and said third bridge; at least one second tab that extends laterally outwardly from said second bridge towards said third bridge, said at least one second tab being spaced from both said at least one second beam and said third bridge; and at least one third tab that extends laterally from said third bridge towards said second bridge, said at least one third tab being spaced from said at least one second beam, said at least one second bridge and said at least one second tab;

an electrode is mounted to said at least one second tab and an electrode is mounted to said at least one third tab; and said electrode array is wrapped around said core so that: said at least second beam is wrapped around a second side surface of said core that is separate from the first side surface of said core; said third bridge is at least partially located between the side surfaces of said core; said at least one second tab projects away from a first end of said at least one second beam and a first end of the second side surface of said core; and said at least one third tab projects away from a second end of said at least one second beam and a second end of the second side surface of said core.

5. The electrode array and delivery assembly of claim 1, wherein:

said electrode array is formed to have: a third longitudinally extending bridge that is separate from said first bridge and said second bridge; at least one second beam formed from elastic material that extends laterally between said second bridge and said third bridge; at least one second tab that extends laterally outwardly from said second bridge towards said third bridge, said at least one second tab being spaced from both said at least one second beam and said third bridge; at least one third tab that extends laterally from said third bridge towards said second bridge, said at least one third tab being spaced from, said at least one second beam, said at least one second bridge and said at least one second tab;

an electrode is mounted to said at least one second tab and an electrode is mounted to said at least one third tab; and said core and said electrode array are collectively shaped so that when said electrode array is wrapped around said core: said at least second beam is wrapped around a second side surface of said core that is separate from the first side surface of said core; said third bridge is at disposed against said first bridge; said at least one second tab projects away from a first end of said at least one second beam and a first end of the second side surface of said core; and said at least one third tab projects away from a second end of said at least one second beam and a second end of the second side surface of said core.

6. The electrode array and delivery assembly of claim 1, wherein the first side surface of said core is curved.

7. The electrode array and delivery assembly of claim 1 wherein:

said core is formed so that, in cross sectional planes perpendicular to longitudinal axis of said core, said core has opposed top and bottom sections that extend between opposed side surfaces of said core and the first side surface is a curved surface;

and said electrode array is wrapped around said core so that said first bridge is disposed over one of the top or bottom sections of said core, said second bridge is disposed over the other of said bottom or top section of said core.

8. The electrode array and delivery assembly of claim 1, wherein a plurality of said steering cables are disposed in said sheath.

9. The electrode array and delivery assembly of claim 1, wherein:

said sheath has a longitudinal axis that extends distally to proximally through said sheath and, in cross sections perpendicular to the longitudinal axis of said sheath, the sheath has a relatively short minor axis and a relatively long major axis; and said at least one steering cable is disposed in said sheath adjacent one end of the major axis of said sheath.

10. The electrode array and delivery assembly of claim 1, wherein:

said sheath has a longitudinal axis that extends distally to proximally through said sheath and, in cross sections perpendicular to the longitudinal axis of said sheath, the sheath has a relatively short minor axis and a relatively long major axis; and at least two said steering cables are disposed in said sheath so that said steering cables are located adjacent opposed ends of the major axis of said sheath.

11. The electrode array and delivery assembly of claim 1, wherein said sheath is formed to define: a central lumen in which said core and said electrode array are disposed; and at least one supplemental bore separate from the central lumen in which said at least one steering cable is disposed.

12. The electrode array and delivery assembly of claim 1, wherein, within said sheath, a portion of said at least one steering cable is encased in material that inhibits the flexing of said cable and a portion of said steering cable is not encased in the material that inhibits the flexing of said steering cable.

13. The electrode array and delivery assembly of claim 1, wherein said core is formed from at least two parallel members.

14. The electrode array and delivery assembly of claim 1, wherein:
   said sheath is formed to have: an inner surface that defines a center lumen in which said core and said electrode array are disposed and; at least one rib that extends inwardly from the inner surface so as to project into the center lumen; and
   said at least one steering cable is disposed in the at least one rib internal to said sheath.

15. The electrode array and delivery assembly of claim 1 wherein:
   said electrode array is formed to have a plurality of longitudinally spaced apart said first tabs that extend outwardly from said first bridge towards said second bridge and said at least one first beam is located between and spaced from two adjacent first tabs; and
   separate said electrodes are mounted to at least two of the said first tabs.

16. The electrode array and delivery assembly of claim 1, wherein said electrode array is formed so that a plurality of longitudinally spaced apart said first beams extend between said first bridge to said second bridge.

17. The electrode array and delivery assembly of claim 1, wherein said electrode array is formed so that:
   a plurality of longitudinally spaced apart said first beams extend between said first bridge to said second bridge; and
   said at least one first said tab is located between and spaced longitudinally away from a pair of longitudinally adjacent said first beams.

18. An electrode array and delivery assembly, said assembly comprising:
   a core formed from flexible material, said core having a longitudinal axis that extends proximally to distally, and at least two opposed side surfaces that are laterally spaced apart from each other wherein, one of the side surfaces is a first side surface;
      an electrode array separate from said core, said electrode array including: first and second bridges that, longitudinally, extend proximally to distally and that are laterally spaced apart from each other; at least one first beam formed from elastic material that extends laterally between said first bridge and said second bridge so as to connect said bridges together; at least one first tab that extends laterally outwardly from said first bridge, wherein said at least one first tab extends laterally towards said second bridge and is separate from both said second bridge and said at least one first beam; at least one second tab that extends laterally outwardly from said second bridge towards said first bridge and is separate from said first bridge, said at least one first tab and said at least one first beam; an electrode mounted to said at least one first tab; and an electrode mounted to said at least one second tab wherein, said electrode array is wrapped around said core so that: said first bridge and second bridge are at least partially located in separate spaces between the spaced apart side surfaces of said core so that said bridges at least partially overlap each other; said at least one first beam is wrapped around the first side surface of said core; said at least one first tab projects away from a first end of said at least one first beam and a first end of the first side surface of said core; and said at least one second tab projects away from a second end of said at least one first beam and a second end of the first side surface of said core;
   a sheath disposed over said core and said electrode array so as to prevent unwrapping of said electrode array from said core; and
   at least one steering cable disposed in said sheath and anchored to said sheath so as to selectively flex said sheath, and
   wherein said sheath is removably disposed over said core and said electrode array so that the extraction of said sheath away from said core and said electrode array allows the release of energy in said at least one first beam so that said at least one first beam unwraps said electrode array from said core so that said core can be withdrawn away from the unwrapped electrode array.

19. The electrode array and delivery assembly of claim 18, wherein:
   said second bridge has first and second opposed longitudinally extending sides, the first side of said second bridge being directed towards said first bridge;
   said at least one second tab extends outwardly from the first side of said second bridge towards the first said bridge;
   said second bridge is formed so as to have at least one third tab, said at least one third tab extending outwardly from the second side of said second bridge;
   an electrode is mounted to said at least one third tab; and
   said core and said electrode array are collectively dimensioned so that when said electrode array is wrapped around said core, said at least one second tab extends away from the first side surface of said core and said at least one third tab extends away from a second side surface of said core.

20. The electrode array and delivery assembly of claim 18, wherein:
   said electrode array is formed to have: a third longitudinally extending bridge that is separate from said first bridge and said second bridge; at least one second beam formed from elastic material that extends laterally between said second bridge and said third bridge; at least one third tab that extends laterally outwardly from said second bridge towards said third bridge, said at least one third tab being spaced from both said at least one second beam and said third bridge; at least one fourth tab that extends laterally from said third bridge towards said second bridge, said at least one fourth tab being spaced from said at least one second beam, said second bridge and said at least one third tab;
   an electrode is mounted to said at least one third tab and an electrode is mounted to said at least one fourth tab; and
   said electrode array is wrapped around said core so that: said at least one second beam is wrapped around a second side surface of said core that is separate from the first side surface of said core; said third bridge is at least partially located between the side surfaces of said core; said at least one third tab projects away from a first end of said at least one second beam and a first end of the second side surface of said core; and said at least one fourth tab projects away from a second end of said at least one second beam and a second end of the second side surface of said core.

21. The electrode array and delivery assembly of claim 18, wherein the first side surface of said core is curved.

22. The electrode array and delivery assembly of claim 18, wherein:
said core is formed so that, in cross sectional planes perpendicular to longitudinal axis of said core, said core has opposed top and bottom sections that extend between opposed side surfaces of said core and the first side surface is a curved surface; and
said electrode array is wrapped around said core so that said first bridge is disposed over one of the top or bottom sections of said core, said second bridge is disposed over the other of said bottom or top section of said core.

23. The electrode array and delivery assembly of claim 18, wherein a plurality of said steering cables are disposed in said sheath.

24. The electrode array and delivery assembly of claim 18, wherein:
said sheath has a longitudinal axis that extends distally to proximally through said sheath and, in cross sections perpendicular to the longitudinal axis of said sheath, the sheath has a relatively short minor axis and a relatively long major axis; and
said at least one steering cable is disposed in said sheath adjacent one end of the major axis of said sheath.

25. The electrode array and delivery assembly of claim 18, wherein said sheath is formed to define: a center lumen in which said core and said electrode array are disposed; and a supplemental bore separate from the center lumen in which said at least one steering cable is disposed.

26. The electrode array and delivery assembly of claim 18, wherein said core is formed from at least two parallel members.

27. The electrode array and delivery assembly of claim 18, wherein:
said electrode array is formed to have: a plurality of longitudinally spaced apart said first tabs that extend outwardly from said first bridge towards said second bridge; a plurality of longitudinally spaced apart second tabs that extend outwardly from said second bridge towards said first bridge and is further formed so that said at least one first beam is, at the first end of said beam, located between and spaced from two adjacent said first tabs and, at the second end of said beam, located between two adjacent said second tabs; and
separate said electrodes are mounted to at least two of the said first tabs and to at least two of the said second said tabs.

28. The electrode array and delivery assembly of claim 18, wherein said electrode array is formed so that a plurality of longitudinally spaced apart said first beams extend between said first bridge to said second bridge.

29. The electrode array and delivery assembly of claim 18, wherein said electrode array is formed so that:
a plurality of longitudinally spaced apart said first beams extend between said first bridge to said second bridge; and
said at least one first said tab is located between and spaced longitudinally away from a pair of longitudinally adjacent said first beams.

* * * * *